United States Patent [19]

Minter

[11] Patent Number: 5,922,574
[45] Date of Patent: Jul. 13, 1999

[54] METHOD FOR PRODUCING COPIES OF A NUCLEIC ACID USING IMMOBILIZED OLIGONUCLEOTIDES

[75] Inventor: Stephen John Minter, New Mills, United Kingdom

[73] Assignee: Tepnel Medical Limited, Cheshire, United Kingdom

[21] Appl. No.: 08/562,075

[22] Filed: Nov. 22, 1995

[30] Foreign Application Priority Data

May 28, 1994 [GB] United Kingdom .................... 9410804
Feb. 2, 1995 [GB] United Kingdom .................... 9502079

[51] Int. Cl.$^6$ ............................... C12P 19/34; C12Q 1/68
[52] U.S. Cl. ............................ 435/91.1; 435/91.2; 435/6
[58] Field of Search ............................ 435/6, 5, 4, 91.1, 435/91.2; 536/23.1, 24.3–24.33

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 4,800,159 | 1/1989 | Mullis et al. | 435/172.3 |
| 5,066,584 | 11/1991 | Gyllensten et al. | 435/6 |
| 5,210,015 | 5/1993 | Gelfand et al. | 435/6 |
| 5,219,727 | 6/1993 | Wang et al. | 435/6 |
| 5,641,658 | 6/1997 | Adams et al. | 435/91.2 |

FOREIGN PATENT DOCUMENTS

| | | |
|---|---|---|
| A-0-184-056 | 11/1986 | European Pat. Off. . |
| A-0-297-379 | 4/1989 | European Pat. Off. . |
| A-0-328-829 | 8/1989 | European Pat. Off. . |
| A-0-356-838 | 3/1990 | European Pat. Off. . |
| A-0-374-665 | 6/1990 | European Pat. Off. . |
| A-0-388-171 | 9/1990 | European Pat. Off. . |
| A-0-455-905 | 11/1991 | European Pat. Off. . |
| A-0-487-104 | 5/1992 | European Pat. Off. . |
| WO-86/07281 | 12/1986 | WIPO . |
| WO-89-09282 | 10/1989 | WIPO . |
| WO-90/06042 | 6/1990 | WIPO . |
| WO-90/09455 | 8/1990 | WIPO . |
| WO 91/14002 | 9/1991 | WIPO . |
| WO-93/03052 | 2/1993 | WIPO . |
| WO-93/04199 | 3/1993 | WIPO . |
| WO-93/09250 | 5/1993 | WIPO . |
| WO-93/13220 | 7/1993 | WIPO . |
| WO-93/15228 | 8/1993 | WIPO . |
| WO-94/09156 | 4/1994 | WIPO . |

OTHER PUBLICATIONS

Mar. 15, 1994 Genetic Engineering News, vol. 14, No. 6, pp. 1, 14 and 19.

*Primary Examiner*—Lisa B. Arthur
*Attorney, Agent, or Firm*—Seed and Berry LLP

[57] ABSTRACT

Amplification of nucleic acids using oligonucleotides immobilized on solid phase supports is disclosed. Target nucleic acid strands (in a sample to be analyzed) are hybridized to the oligonucleotides and copy target strands (incorporating immobilized oligonucleotide) are produced using the target strands as templates. The target strands are denatured from the copy target strands and rehybridized to non-extended oligonucleotides. In the next step, new copy target 1 strands are synthesized from the oligonucleotides hybridized to the target strands, and simultaneously copy target 2 strands are synthesized using previously generated copy target 1 strands. Sequence of denaturing, rehybridizing, and producing copy target 1 and copy target 2 strands is repeated as often as necessary to give the desired degree of amplification.

19 Claims, 18 Drawing Sheets

METHOD FOR PRODUCING COPIES OF A NUCLEIC ACID USING IMMOBILIZED OLIGONUCLEOTIDES

BACKGROUND OF THE INVENTION

The present invention relates to a method of producing copies of at least part of a nucleic acid strand.

In the field of genetic engineering, it is often the case that only a very small amount of a nucleic acid is present in a sample but that a somewhat larger amount of the full or part of the sequence is required for the purposes of research or a diagnostic test. Alternatively, it may be necessary to know whether or not a particular nucleic acid is present at all in a sample (e.g. to determine whether a person has been infected by a particular virus, either DNA or RNA, or has a particular sequence, present or absent, in their nucleic acid). Since the amount of the nucleic acid, if present in the sample, would be below detectable limits, it is necessary to subject the sample to an amplification reaction such that an enhanced amount of the nucleic acid (if present) is produced. A test may then be conducted to determine the presence or otherwise of the nucleic acid. If the test is positive then this confirms that the nucleic acid was present in the original sample. Conversely if the test is negative then this is confirmation that the nucleic acid was not present in the original sample.

SUMMARY OF THE INVENTION

The present invention relates to various techniques by means of which enhanced amounts of nucleic acids present or potentially present in a sample may be produced.

According to a first aspect of the present invention there is provided a method of producing copies of at least part of a nucleic acid strand (the "target strand") present or potentially present in a sample, the method comprising the steps of (i) providing a solid support system having immobilised thereon a plurality of single stranded oligonucleotides which are capable of hybridising to the target strands, (ii) providing the target strands in single stranded form and hybridising the target strands to oligonucleotides on the support, the number of oligonucleotides substantially exceeding the number of target strands, (ii)(a) washing the support system to remove non-hybridised material, (iii) producing copy target 1 strands which incorporate the immobilised oligonucleotides and include a nucleic acid sequence complementary to at least part of the target strand, said copy target 1 strands being produced at least partially by using the target strand as a template to generate at least part of the copy target 1 sequence, and, if necessary, completing formation of the copy target 1 sequence (iv) denaturing the strands hybridised to the copy target 1 strands and optionally rehybridising at least some of the former strands to oligonucleotides on the support which have not been converted to copy target 1 strands, (v) simultaneously,
  (a) using the copy target 1 strands immobilised on the solid support as templates to generate (from primers hybridised to the copy target 1 strands) copy target 2 strands which comprise the nucleic acid sequence of interest, and
  (b) using the target strands if they have been hybridised to the immobilised oligonucleotides as templates to generate at least part of further copy target 1 strands, and (if necessary) completing formation of the copy target 1 strands, and (vi) repeating steps (iv) and (v) as many times as required, each repeat of steps (iv) and (v) using copy target 2 strands to generate further copy target 1 strands.

As indicated previously, the method of the invention may be effected on a sample which may or may not contain the nucleic acid of interest. If the nucleic acid is not present then it will be appreciated that the steps (iii)–(vi) outlined above do not lead to the production of copy target 1 and copy target 2 strands. Nevertheless the fact that copy target 2 strands are not produced provides valuable information since a negative result in a detection procedure effected to determine the presence of copy target 2 strands confirms that the target strand was not present in the original sample.

The washing step (ii)(a) ensures that non-hybridised material is removed from the support system so that a clean sample of the target strand is present on the solid support system for use in step (iii). Therefore contaminants which may be present in the original sample do not take part in the method of the invention.

In step (iv), the target strands may be rehybridised to non-extended oligonucleotides on the support. Alternatively the original target strands may be removed from the solid support system prior to step (v).

It is also preferred that the solid support system is washed and/or reagents removed after each hybridisation reaction and/or after each strand synthesis reaction and/or ligation reaction effected within this overall sequence of steps (iii)–(vi). Thus, for example, excess primers introduced at step v(b) may be removed prior to generation of (at least part of further) copy target 1 strands The oligonucleotides are preferably covalently linked to the solid support. Preferably the solid support system is a particulate system and the oligonucleotides are immobilised on the particles. The use of a particulate support system is an important feature in its own right and therefore according to a second aspect of the invention there is provided a method of producing copies of at least part of a nucleic acid strand (the "target strand") present or potentially present in a sample, the method comprising the steps of (i) providing a particulate solid support system having immobilised thereon a plurality of single stranded oligonucleotides which are capable of hybridising to the target strands, (ii) providing the target strands in single stranded form and hybridising the target strands to oligonucleotides on the support, the number of oligonucleotides substantially exceeding the number of target strands, (iii) producing copy target 1 strands which incorporate the immobilised oligonucleotides and include a nucleic acid sequence complementary to at least part of the target strand, said copy target 1 strands being produced at least partially by using the target strand as a template to generate at least part of the copy target 1 sequence, and, if necessary, completing formation of the copy target 1 sequence, (iv) denaturing the strands hybridised to the copy target 1 strands and optionally rehybridising at least some of the former strands to oligonucleotides on the support which have not been converted to copy target 1 strands, (v) simultaneously,
  (a) using the copy target 1 strands immobilised on the solid support as templates to generate (from primers hybridised to the copy target 1 strands) copy target 2 strands which comprise the nucleic acid sequence of interest, and (b) using the target strands if they have been hybridised to the immobilised oligonucleotides as templates to generate at least part of further copy target 1 strands, and (if necessary) completing formation of the copy target 1 strands, and (vi) repeating steps (iv) and (v) as many times as required, each repeat of steps (iv) and (v) using copy target 2 strands to generate further copy target 1 strands.

It is a preferred feature of the second aspect of the invention that, after step (ii), the particulate solid supports are washed to remove non-hybridised material prior to execution of step (iii).

The particles are preferably of non-porous silica and preferably have a size of 50 to 200 (more preferably 100 to 200) microns. These particles may have a cross-linked siloxane matrix having reactive groups (e.g. epoxy groups) which may be reacted with an oligonucleotide to effect immobilisation thereof onto the support via the siloxane matrix. Suitable particles are as described in WO-A-93/13220 (Tepnel).

It is highly preferred that the solid supports are packed into a column into and from which liquids may be readily introduced and removed. The use of such a column enables reagents (e.g. hybridisation buffers, nucleotide) to be readily introduced into the reaction system. Furthermore after any one stage this column may easily be washed to remove excess reagents etc. so as to leave a 'clean' sample on the column for effecting the next stage.

A suitable column arrangement is disclosed in WO-A-93/13220.

In the above procedure, the copy target 1 strands may be generated in a number of ways. Firstly, the orientation of the oligonucleotide on the support may be such that it serves, in effect, as a primer which may be extended in step (v)(b) (using the target strands or copy target 2 strand hybridised thereto as a template) so as directly to produce the copy target 1 stand. Secondly, the orientation of the oligonucleotide may be such that it cannot be extended in the manner specified in the previous sentence. In this case, it is necessary to add a separate primer which will hybridise to the copy target or copy target 2 strand hybridised to the immobilised oligonucleotide and then (using the target as a template) extend this strand back towards the oligonucleotide to which it is then subsequently joined to complete preparation of the copy target 1 strand.

It is a feature of the method of the invention that, in step (ii), there are substantially more oligonucleotides on the solid support system than there are target strands to hybridise thereto. By substantially more we mean that the total number of oligonucleotides on the support will exceed the number of target strands introduced at step (ii) preferably by a factor of at least 10, more preferably a factor of at least 100, and even more preferably by a factor of at least 1000.

Step (v)(a) leads to the production of copy target 2 strands which comprise the nucleic acid sequence of interest. At the end of step (v) (which will involve the use of solution phase primers in addition to the oligonucleotides immobilised on the support), the copy target 2 strands are hybridised to the copy target 1 strands and, after the first execution of step (v), the number of copy target 2 strands is relatively low compared to the number of non-extended oligonucleotides. Therefore in the first repeat of step (iv), the copy target 2 strands (which have been denatured from the copy target 1 strands) will tend to hybridise to non-extended oligonucleotides rather than re-hybridise to copy target 1 strands. Thus in the repeat of step (v)(b) the copy target 2 strands hybridised to oligonucleotides serve to generate further copy target 1 strands whilst further copy target 2 strands are simultaneously produced (from previously produced copy target 1 strands) in step (v)(a).

Steps (iv) and (v) are repeated as often as required. During at least the early cycles of the process, each repeat of step (v) will produce an increasing number of copy target 2 strands and there will, of course, be a decreasing number of non-extended oligonucleotides. These early stages provide a generally geometric increase in the number of copy target 2 strands produced. During each subsequent repeat of step (iv) there is an increasing likelihood of copy target 2 strands rehybridising to copy target 1 strands and these combinations do not lead to production of further copy target 1 or copy target 2 strands. Provided that steps (iv) and (v) are repeated sufficiently often, there will come a point at which all or substantially all of the original oligonucleotides present on the support are extended to produce copy target 1 strands. It is preferred that the reaction is effected so that this point is reached.

The product of step (f) comprises the solid support system having double stranded nucleic acid immobilised thereto. More particularly each double strand comprises, as one strand, a copy target 1 strand incorporating the original oligonucleotides immobilised on the support and, hybridised thereto as the other strand, a copy target 2 strand incorporating a copy of the sequence of interest from the original target strand. The actual extent to which the original sequence is reproduced will depend for example on (i) the region of the target strand which hybridises to the oligonucleotide in step (ii), and (ii) the region of the copy target 1 strand to which the primer hybridises in step e(i)).

The product of step (f) may be used in a number of ways. Firstly the copy target 2 strands may be denatured from the immobilised copy target 1 strands so as to obtain for collection an enhanced amount (compared to the amount of the original target) of the sequence of interest. Once the copy target 2 strands have been denatured and removed from the system, there remains a solid support system which may be used at least once for generating further amounts of the sequence of interest by a procedure which comprises (vii) hybridising primers to the copy target 1 strands at locations such that extension products of the primers using the copy target 1 strands as templates incorporate the sequence of interest, (viii) extending the primers using the copy target 1 strands as templates, and (ix) denaturing the product strands from the copy target 1 strands and collecting the product strand.

Preferably steps (vii)–(ix) are repeated at least once and preferably a plurality of times. Each repeat of steps (vii)–(ix) produces substantially the same amount of the product strand. Therefore, on a cumulative basis, repeats of steps (vii)–(ix) produce linearly increasing amounts of the product strand. To maximise the amount of product strand obtained it is obviously desirable that all or substantially all of the original oligonucleotides are converted to copy target 1 strands.

An alternative use for the product obtained from step (vi) (or that obtained from step (viii)) is to use a restriction enzyme to cleave the double stranded product from the support. The double stranded product may be cloned into a vector or used in any other way.

It will be appreciated that nucleic acids produced by the method of the invention may be detected by conventional means, e.g. by means of an enzyme labeled oligonucleotide capable of hybridising to the nucleic acid.

The method of the invention may be effected in a number of ways.

In a first embodiment, the oligonucleotides are immobilised to the solid support system in an orientation such that, when the target strand is hybridised thereon and using the appropriate enzyme system, the oligonucleotides are themselves extended to produce the copy target 1 strands. This will generally imply that the oligonucleotides are bonded via their 5' ends to the solid support system so that extension of the oligonucleotide proceeds in 5' to 3' direction.

In this embodiment, the primers as employed in step (v)(a) for producing copy target 2 strands are solution phase primers which are hybridised to the copy target 1 strand at locations remote from the support and extended back towards the support to produce the copy target 2 strands. It will of course be appreciated that, during production of the copy target 2 strands, further copy target 1 strands (immobilised to the support) are produced by extension of the immobilised oligonucleotides.

In its simplest implementation, the first embodiment of the invention employs a solid support system incorporating one type of immobilised oligonucleotides (for hybridising one target strand of a double stranded sequence). In a development of the first embodiment of the invention, the solid support system incorporates two different immobilised oligonucleotides, one oligonucleotide being such that it will hybridise to one of the strands of a double stranded nucleic acid and the other oligonucleotide being such that it will hybridise to the other strand of the nucleic acid. It will be appreciated that, with this development, it is possible to produce two types of copy target 2 strands which are complementary to each other and which (when hybridised together) reproduce at least a portion of the original double stranded sequence.

In a second embodiment of the invention, the oligonucleotides are immobilised to the solid support system in an orientation such that, when the target strand is hybridised thereto, primers may be hybridised to the target strand and (using the appropriate enzyme system) extended back towards the oligonucleotides. In this case, it is necessary to complete preparation of the copy target 1 strands by ligating the primer extension product to the oligonucleotide. This embodiment of the invention will generally imply that the oligonucleotides are bonded via their 3' ends to the solid support system so that extension of the primer (hybridised to the target strand) proceeds in the 5' to 3' direction back towards the support.

For the second embodiment of the invention, the solid support system may incorporate either a single type of immobilised oligonucleotide or two types of immobilised oligonucleotide such that complementary copy target 2 sequences may be produced.

It is also possible (in accordance with a third embodiment of the invention) to combine the first and second embodiments of the invention such that the solid support system incorporates two immobilised oligonucleotides, namely (i) a first oligonucleotide which may itself be extended to produce a copy target 1 strand (as for the first embodiment of the invention) and (ii) a second oligonucleotide which (for the purposes of producing a copy target 1 strand) requires to be ligated to an extension product of a primer hybridised to the target strand.

As mentioned above, the solid support system may incorporate two different immobilised oligonucleotides, one nucleotide being such that it will hybridise to one of the strands of a double stranded nucleic acid and the other oligonucleotide being such that it will hybridise to the other strand of the nucleic acid. This is an important feature in its own right and therefore according to a third aspect of the present invention there is provided a method of producing copies of at least part of a nucleic acid strand present or potentially present in a sample, the method comprising the steps of (i) providing a solid support system having immobilised thereon a plurality of each of two different single stranded oligonucleotides 0 and 0' each of which is capable of hybridising to a respective one of two complementary strands of a double stranded nucleic acid, said complementary stands providing target 1 and 1' strands, (ii) providing the target 1 and 1' strands in single stranded form and hybridising the target strands to oligonucleotides on the support, the number of oligonucleotides substantially exceeding the number of target strands, (iii) producing copy target 1 and 1' strands each of which incorporates an immobilised oligonucleotide 0 or 0' respectively, and a nucleic acid sequence complementary to at least part of the target 1 or 1' strand respectively, said copy target 1 and 1' strands being produced at least partially by using the respective target strands as templates to generate at least part of the copy target 1 or 1' sequence, and, if necessary, completing formation of the copy target 1 sequence and/or copy target 1' sequence.

(iv) denaturing the strands hybridised to the copy target 1 strands and optionally rehybridising at least some of the former strands to oligonucleotides on the support which have not been converted to copy target 1 strands, (v) simultaneously,
  (a) using the copy target 1 strands immobilised on the solid support as templates to generate (from primers hybridised to the copy target 1 strands) copy target 2 strands which comprise the nucleic acid sequence of interest, and
  (b) using the target strands if they have been hybridised to the immobilised oligonucleotides as templates to generate at least part of further copy target 1 strands, and (if necessary) completing formation of the copy target 1 strands, and (vi) repeating steps (iv) and (v) as many times as required, each repeat of steps (iv) and (v) using copy target 2 strands to generate further copy target 1 strands.

BRIEF DESCRIPTION OF THE DRAWINGS

The invention will be further described by way of example only with reference to the accompanying drawings, in which.

DETAILED DESCRIPTION OF THE INVENTION

Figure 1:
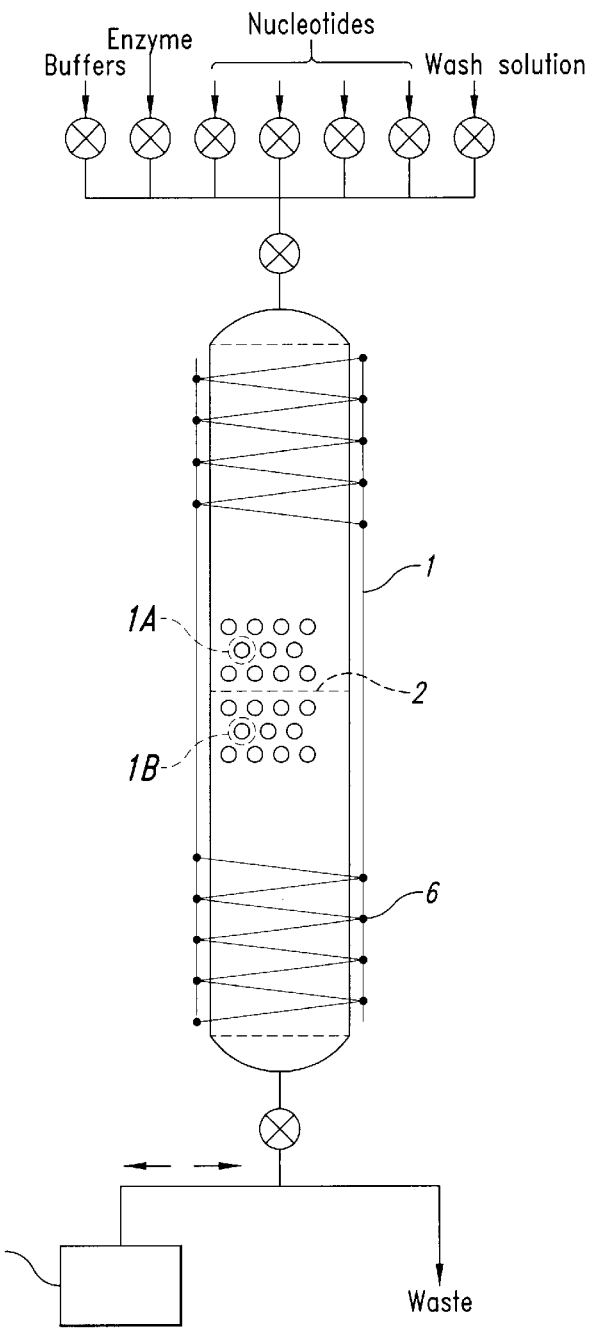
FIGS. 1A and 1B illustrates one embodiment of apparatus in which the method of the invention may be effected.
Figure 1A:
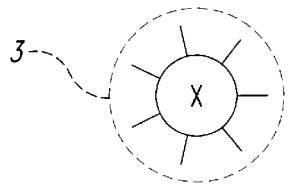
Figure 1B:
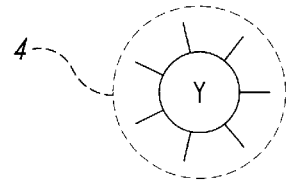

Referring firstly to FIG. 1, the illustrated apparatus comprises a flow through column 1 including a central transverse partition 2 above which are provided particulate supports $P_A$ and below which are provided particulate supports $P_B$. Each of such supports $P_A$ and $P_B$ have oligonucleotides 3 and 4 respectively immobilised thereon as discussed in more detail below. Partition 2 is such that liquids may pass therethrough but not the particles $P_A$ and $P_Y$. It is however equally possible for the partition 2 to be dispensed with and for supports $P_A$ and $P_B$ to be admixed together.

Associated with the column 2 are feed streams for hybridising buffers, enzymes, nucleotides and wash solutions as shown. Further associated with column 2 is a storage arrangement 5 to which product (as described below) may be supplied from the column and from which product may be returned to the column. A heater 6 is also provided for heating column 1 as necessary. Finally, valves are provided as shown for introducing reagents to and from the column as shown. Delivery of liquids into and out of the column may be effected by means of syringes, e.g. positive displacement syringes.

Supports $P_A$ and $P_B$ may be as described in WO-A-93/13220. Thus the supports may be of solid silica provided on its outer surface with a siloxane matrix to which are bonded oligonucleotides 3 and 4 (respectively). The manner in which the oligonucleotides are bonded to the support may be as described in WO-A-93/13220.

Supports $P_A$ and $P_B$ differ only in the oligonucleotides bonded thereto. Consider a molecule of DNA comprised of complementary, hybridised strands A and B. The oligonucleotides immobilised on supports $P_A$ are such that strand A (when denatured from strand B) will hybridise thereto whereas the oligonucleotides on supports $P_B$ are capable of hybridising to strand B.

Figure 2A:
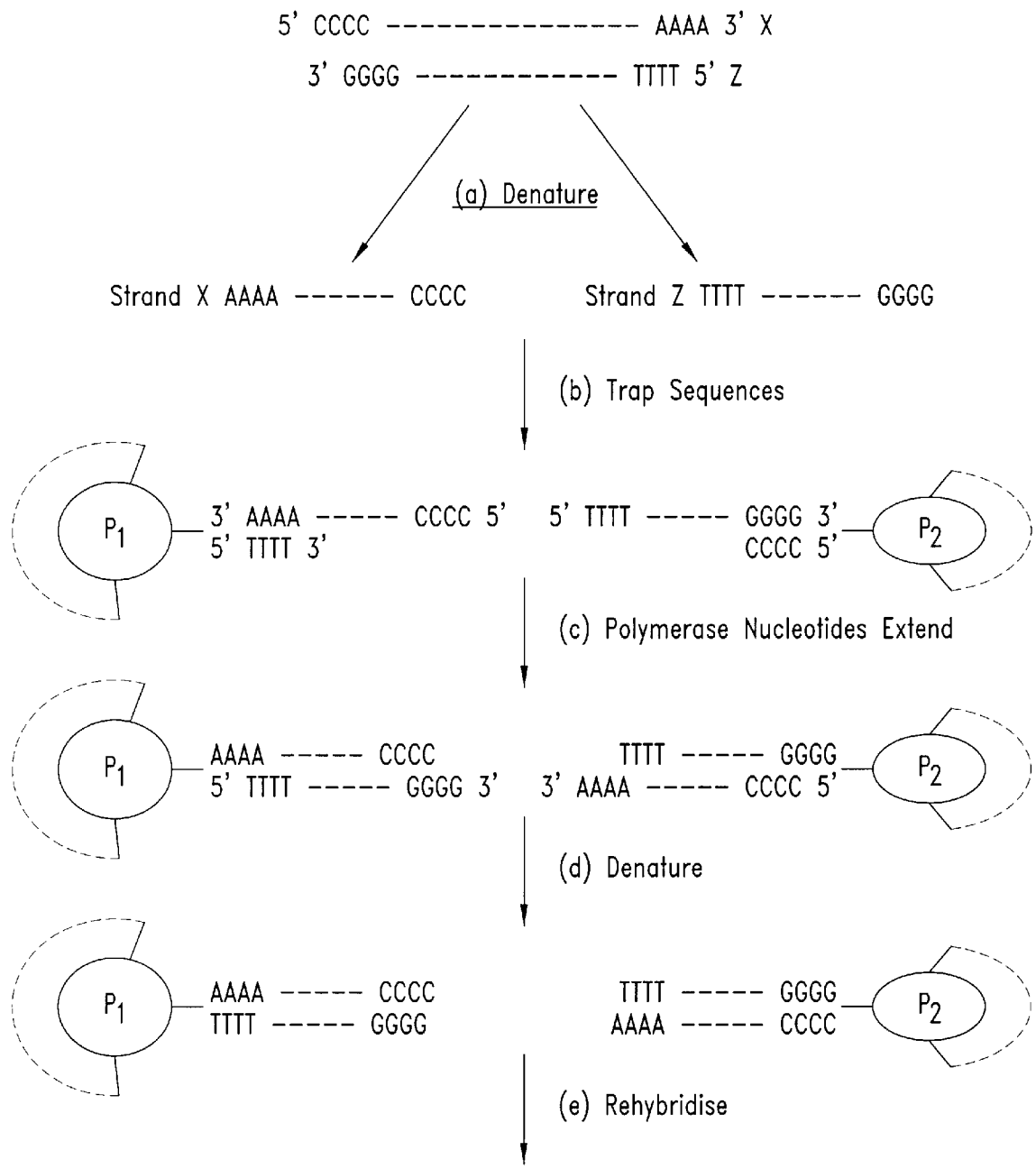
FIGS. 2A and 2B schematically illustrates a procedure in accordance with the first embodiment of the invention.
Figure 2B:
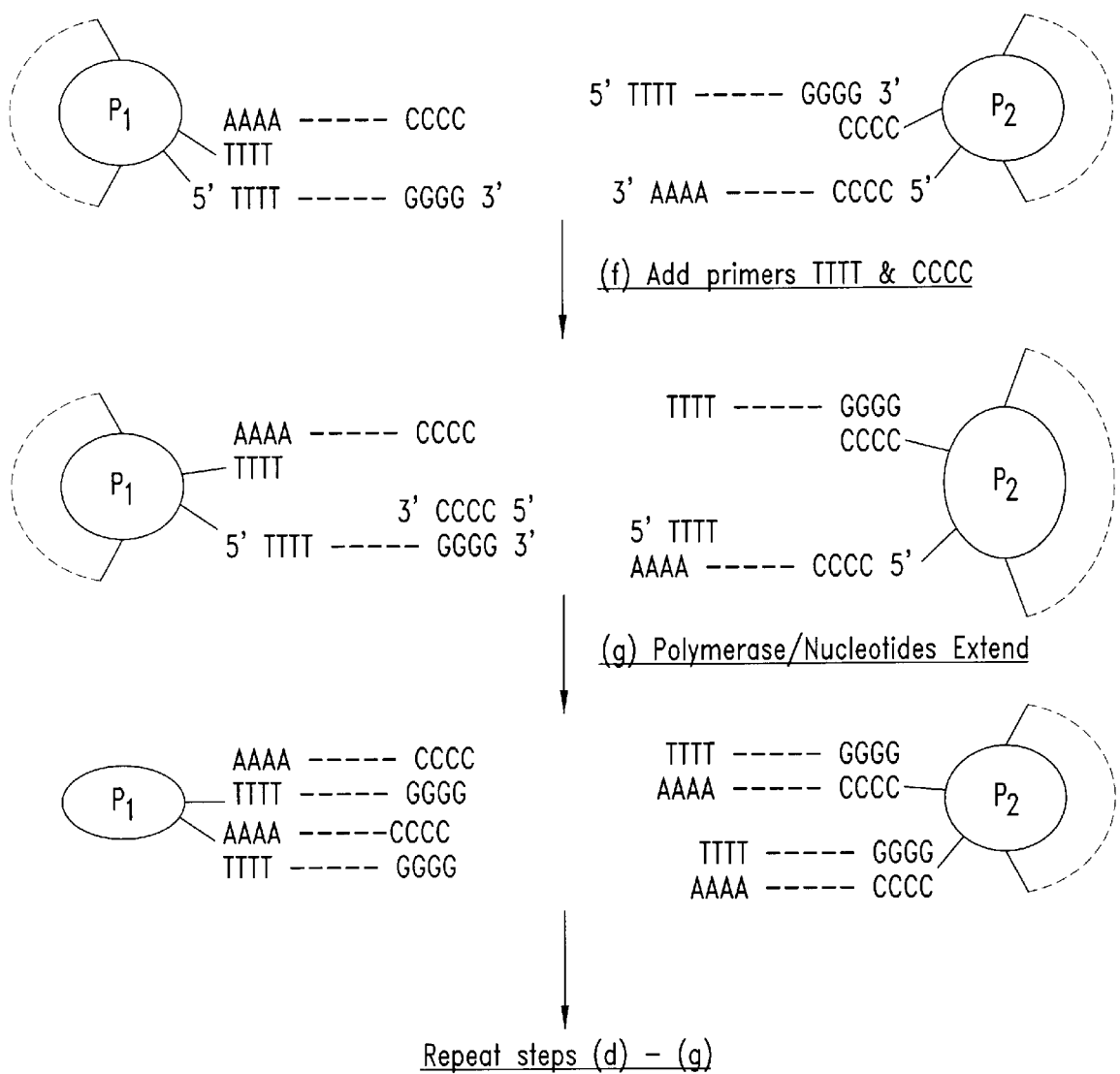

Reference is now made to FIG. 2 which illustrates the use of the first embodiment of the invention for producing copies of a double stranded sequence of interest represented as having individual sequences X and Y. The column includes two types of particles designated in FIG. 2 as P1 and P2. For the purposes of illustration, the strands X and Y are assumed to have the arbitrary base sequences as shown at their end regions.

The steps involved are as follows:

1. The DNA, which contains the target sequence, is either denatured externally to the column and then introduced onto the column or the double stranded DNA is introduced onto the column and then denatured in situ. In both instances the DNA is subjected to elevated temperatures or chemical means known in the art to denature the DNA. For either case, the denatured DNA is mixed with the support within the column. The column is then subjected to a reduction in temperature, to one which allows the hybridisation of the target with the particle bound oligonucleotides. This hybridisation reaction occurs at a very precise temperature which is specific for the combination of support bound sequence and the target sequence (referred to as the Tm (melting temperature) of the reaction). The Tm is governed by the ratio of the bases in the target sequence. High A T ratios melt at lower temperatures than High G C ratio containing DNA (for any given salt concentration).

The 3' end of sequence X (target) is shown as having the sequence AAAA. Particles P1 have immobilised thereto (by their 5' ends) oligonucleotides of sequence TTTT, i.e. a sequence which will hybridise to the 3' end of sequence X whereby this strand may be trapped (step (b)).

Strand Z (target) is shown as having, at its 3' end, the sequence GGGG. Particles P2 have immobilised thereto (by their 5' ends) oligonucleotides having a sequence CCCC which will hybridise to the 3' region of strand Y whereby this strand may be trapped (step (b)).

2. After washing of the column to remove impurities (which will include non target and DNA and proteins which can be inhibitory), lipids and salts, the column is continued to be washed with a buffer which is ideal for the next process in the procedure. A polymerase enzyme and nucleotides are then added so as to extend the column bound oligonucleotides, which are capable of serving as primers, thereby copying the trapped strands (step (c)) from the primer and producing copy target 1 strands immobilised on the support.

3. Once this reaction has been completed, the column may be washed to remove unwanted (unused) reagents.

4. Subsequently, the target strands are denatured from the immobilised copy target 1 strands (step (d)) and are then allowed to rehybridise to non-extended oligonucleotides (step (e)) which are in considerable excess compared to the original amount of the original double stranded molecule.

5. In the next step (step (f)), free (solution phase) primers, having the sequences TTTT and CCCC are added and hybridised as shown to those strands which are covalently linked to the particle P1 or P2. Excess free primers are then removed from the column using a wash step.

6. Enzyme and nucleotides are now added (step (g)) so that for each of particles P1 and P2 two extension reactions occur simultaneously, namely
   (i) extension of those covalently immobilised oligonucleotides (e.g. TTTT for P1) to which a nucleic acid strand is hybridised, (this occurs in a direction away from the supports P1 and P2) producing copy target 1 strands, and
   (ii) extension of the added "free" primers (e.g. primer CCCC for P1) which are hybridised to covalently immobilised strands (this occurs in a direction towards the supports P1 and P2) producing copy target 2 strands.

Step (i) leads to covalently immobilised sequences Z being synthesised on particle P1 and covalently immobilised sequences X being synthesised on particles P2. Step (ii) leads to synthesis of sequences X on particles P1 and sequences Z on particles P2. This is the beginning of geometric copying of the target DNA.

7. The column may then be washed to remove unwanted reagents.

8. The procedure of steps (d)–(g) may be repeated as many times as necessary.

There is an original large excess of immobilised oligonucleotides on the supports. As such, initial cycles of the process will proceed as follows (considering only particle P1). Assume that, at the end of step (g), a particle P1 has 2 covalently immobilised strands Z and two strands X bound by hybridisation to immobilised strands Z. On the first repeat of steps (d)–(g) the corresponding figures will be four of each of strands X and Z. On the next repeat there are 8 of each sequence and so on. However this exponential type increase is limited by the number of immobilised oligonucleotides on the support. Thus the amount of hybridised strands synthesised in step (g) will eventually increase to such a level that during subsequent denaturing and rehybridisation steps (steps (d) and (c)), some strands X will hybridise to non-extended oligonucleotides but others will hybridise to strands Z formed as extensions of immobilised primers. Eventually, all immobilised primers will become extended and the particles P1 become saturated with double stranded nucleic acid. (Similar comments apply to particles P2).

The double stranded acid may be "cut" from the support (using an appropriate restriction enzyme). Alternatively the copy target 2 products may be denatured from the support as obtained in step (g) which may then be used for generation of linearly increasing amounts of the copy target 2 strands by repeating the following sequence of steps.

(i) hybridising primers CCCC and TTTT to the immobilised copy target 1 strands, (ii) extending the primers, and (iii) denaturing and collecting the extension products (i.e. copy target 2 strands).

Figure 3A:
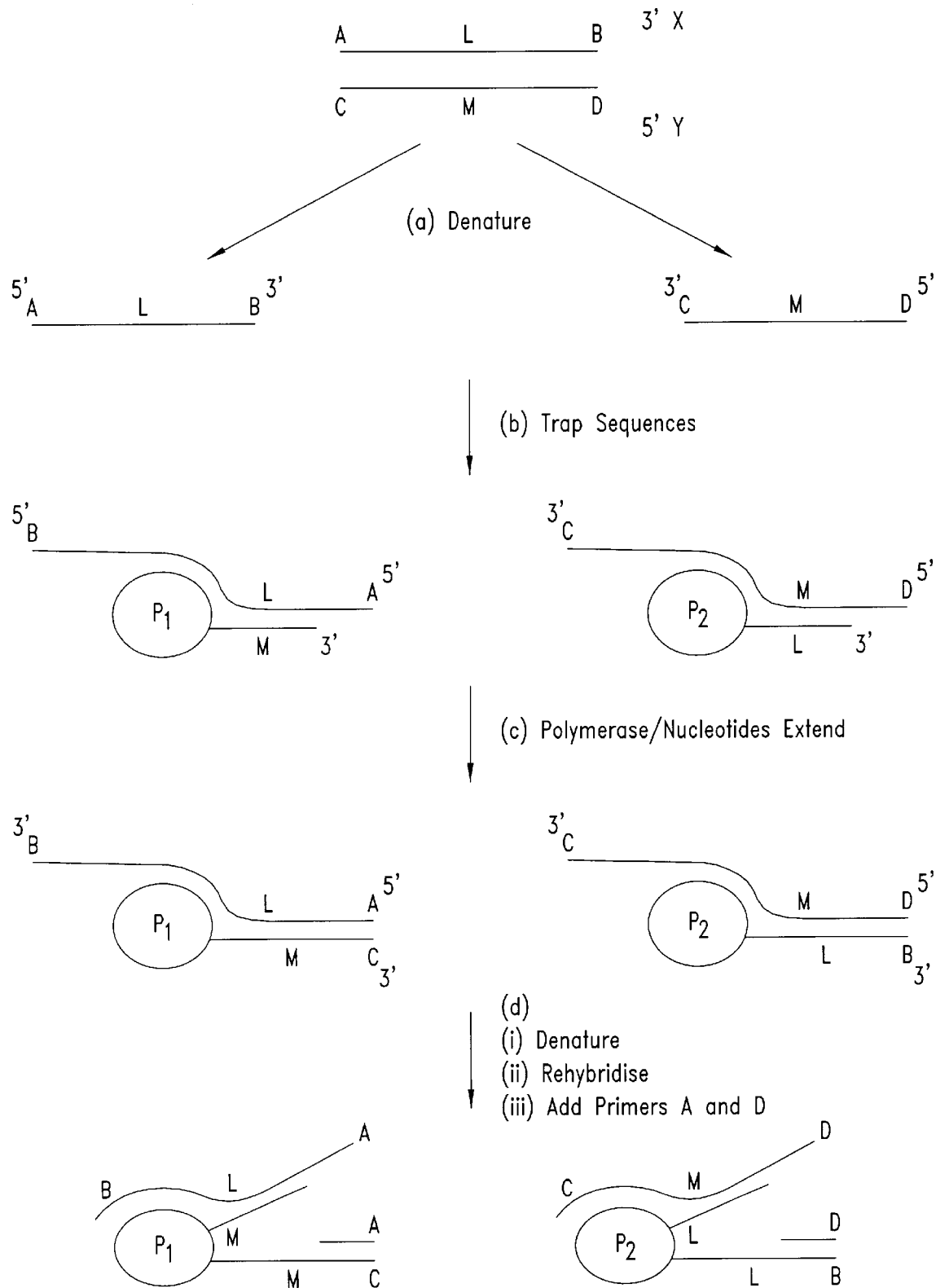
FIGS. 3A and 3B schematically illustrates a further procedure in accordance with the first embodiment of the invention.
Figure 3B:
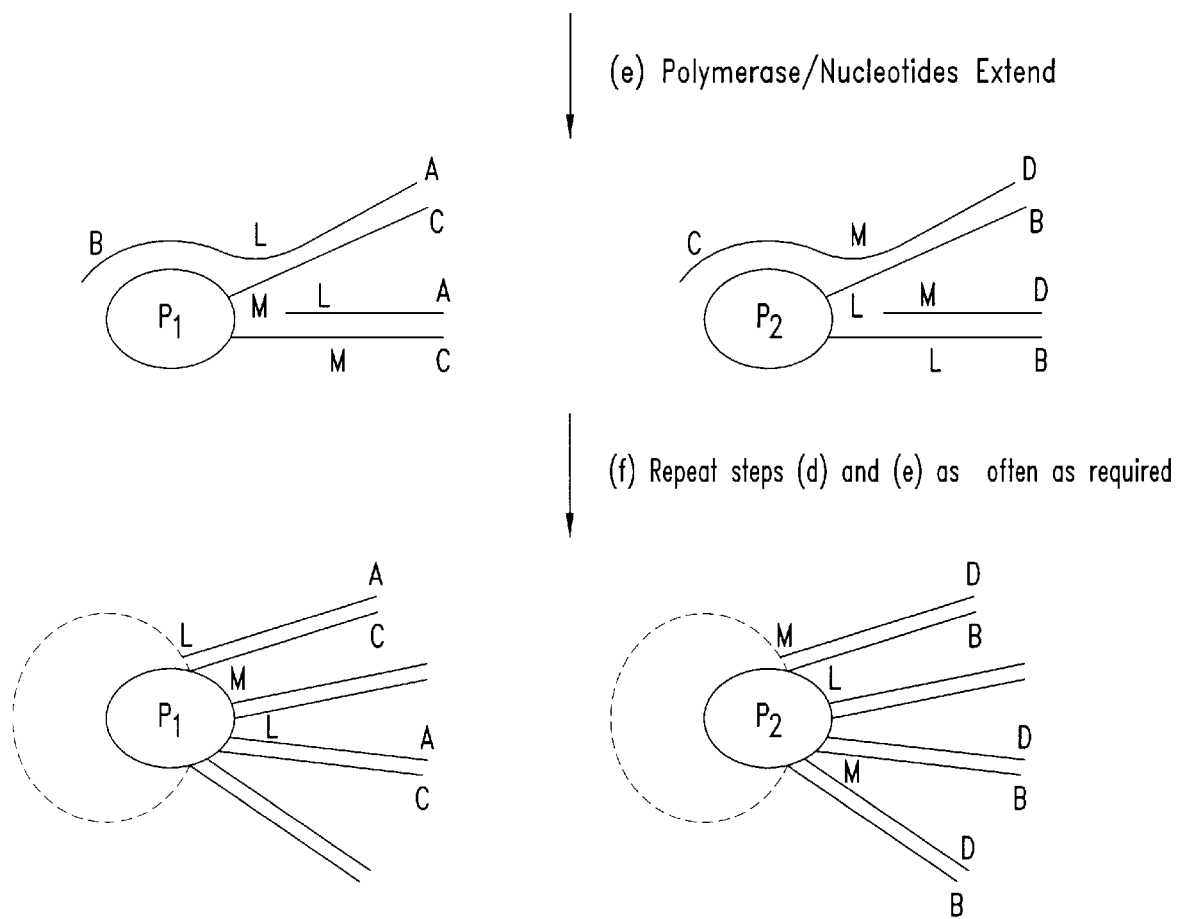

Reference is now made to FIG. 3 which illustrates a modification of the procedure shown in FIG. 2. The procedure of FIG. 3 starts with a double stranded nucleic acid in which one of the strands X has arbitrary terminal sequences A and B as shown at its 5' and 3' ends respectively and the other strand Y has arbitrary terminal sequences C and D (A being complementary to C and B being complementary to D). Between sequences A and B, part of the X strand has a sequence L which is complementary to sequence M on the Y strand.

Two types of particle P1 and P2 are provided. Particle P1 carries a plurality of oligonucleotides of sequence M immobilised (on the particulate P1 supports) via their 5' ends. Particle P2 carries a plurality of oligonucleotides of sequence L immobilised (on the particulate supports P2) via their 5' ends.

The procedure of FIG. 3 involves the same overall sequence of steps as that of FIG. 2 which are therefore not described again in detail. The following points should however be noted.

In the method of FIG. 2, the two immobilised oligonucleotides (TTTT and CCCC) were such that the copy target 1 strands synthesised had complementary base sequences. This was due to the fact that one oligonucleotide (CCCC) corresponded to one end of sequence X and the other oligonucleotide (TTTT) corresponded to the opposite end of sequence Z.

In contrast, in the method of FIG. 3, the strand X is hybridised via its intermediate region L to oligonucleotide M on particle P1 and strand Z is immobilised via its intermediate sequence M to oligonucleotide L on particle P2. During the subsequent extension reaction (step (c)) the copy target 1 product produced on particle P1 has the following sequence

5' M------------C 3' whereas that produced on particle P2 has the sequence

5' L-----------B 3'

Thus the two copy target 1 products are not complementary.

During step (e), particle P1 produces a copy target 2 product of the sequence

3' L--------------------A 5' which represents a copy of a portion of original strand X whereas particle P2 produces copy target 2 product of the sequence

3' M------------------D 5' i.e. a copy of a portion of original strand Z.

Figure 4A:
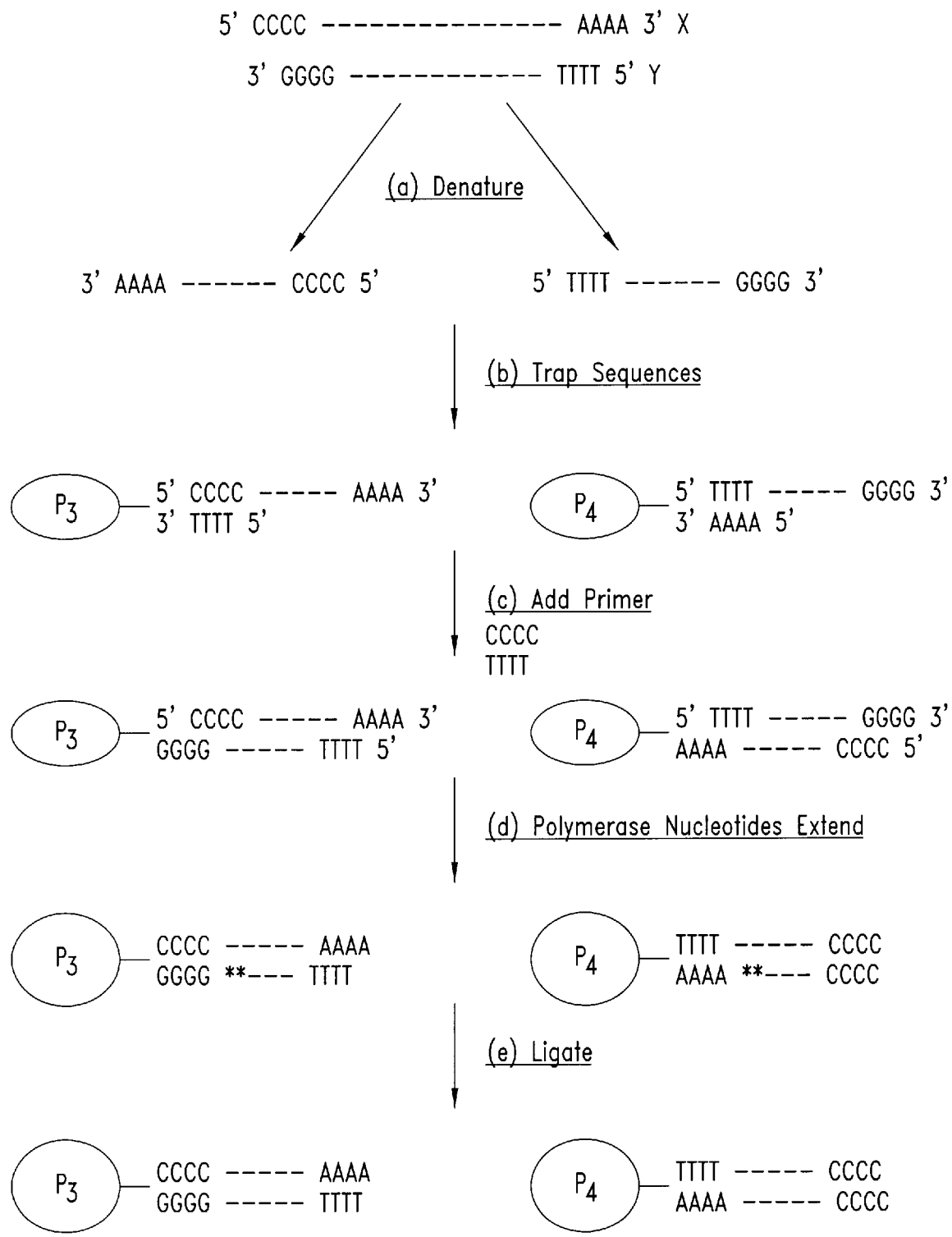
FIGS. 4A and 4B schematically illustrates a procedure in accordance with the second embodiment of the invention.
Figure 4B:
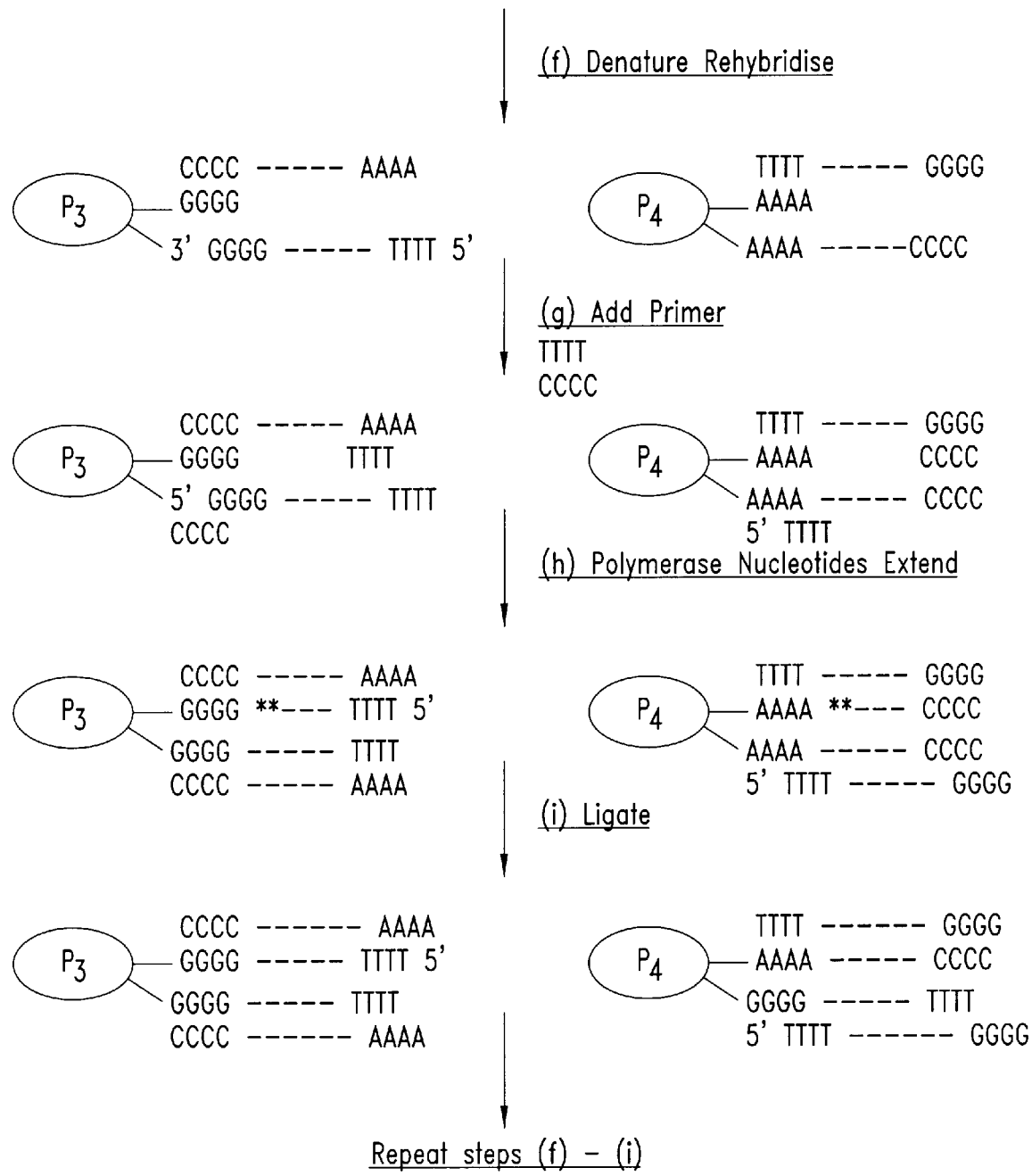

Reference is made to FIG. 4 which illustrates the second embodiment of the invention.

The method starts with double stranded DNA having strands X and Y. Two types of particle P3 and P4 are used on the column.

A first type of particle P3 has immobilised thereto (by its 3' end) an oligonucleotide GGGG which will hybridise to the 5' end region of strand X.

The other type of particle P4 has immobilised thereto (again by its 3' end) an oligonucleotide AAAA which will immobilise to the 5' end region of strand Z.

After denaturation of the target double strand DNA and hybridisation on to the particles P3 and P4, the particles are washed to remove contaminants (as above). The hybridisation reaction traps the sequences of interest.

Two free primers (CCCC and TTTT) are added and hybridised to the particle bound DNA. One such primer (TTTT) will hybridise to the 3' end region of strand X. The other primer (CCCC) will hybridise to the 3' end of immobilised strand Z (step c).

The particles are then washed to remove excess reagent.

Enzymes and nucleotides are added to the column (there is the possibility that this may be performed simultaneously with the primers) and an extension reaction effected so as to extend the primers back towards the supports as far as, but not joined to, the immobilised oligonucleotides (step d). The "**" symbol in the product of step (d) symbolises the fact that the extension product is not joined to the immobilised oligonucleotide.

A DNA ligase is added to ligate the extension products (of the primers) to the immobilised oligonucleotides thereby producing copy target 1 strands immobilised to the supports (step e).

After denaturation and rehybridisation (step f), the two primers TTTT and CCCC are again added. Primer TTTT hybridises to the 3' end of the copy target 1 strand on particle P4 and also to the 3' end of the hybridised nucleic acid on particle P3. Similarly primer CCCC hybridises to the 3' end of the copy target 1 strand immobilised on particle P3 and also to the 3' end of the hybridised nucleic acid on particle P4.

The column is then washed to remove excess reagents. Polymerase and nucleotides are added and an extension reaction is then effected (steps g and h). The primers are extended as shown (producing copy target 2 strands) and (after washing of the column) a ligation reaction is effected to complete preparation of copy target 1 strands on each of supports P3 and P4.

Steps (f)–(i) are repeated as often as necessary to build up the number of copy target 1 and copy target 2 strands. The latter may ultimately be collected as product and the former (immobilised on their supports) may be used for the production of further copy target 2 product in the manner previously described.

Figure 5A:
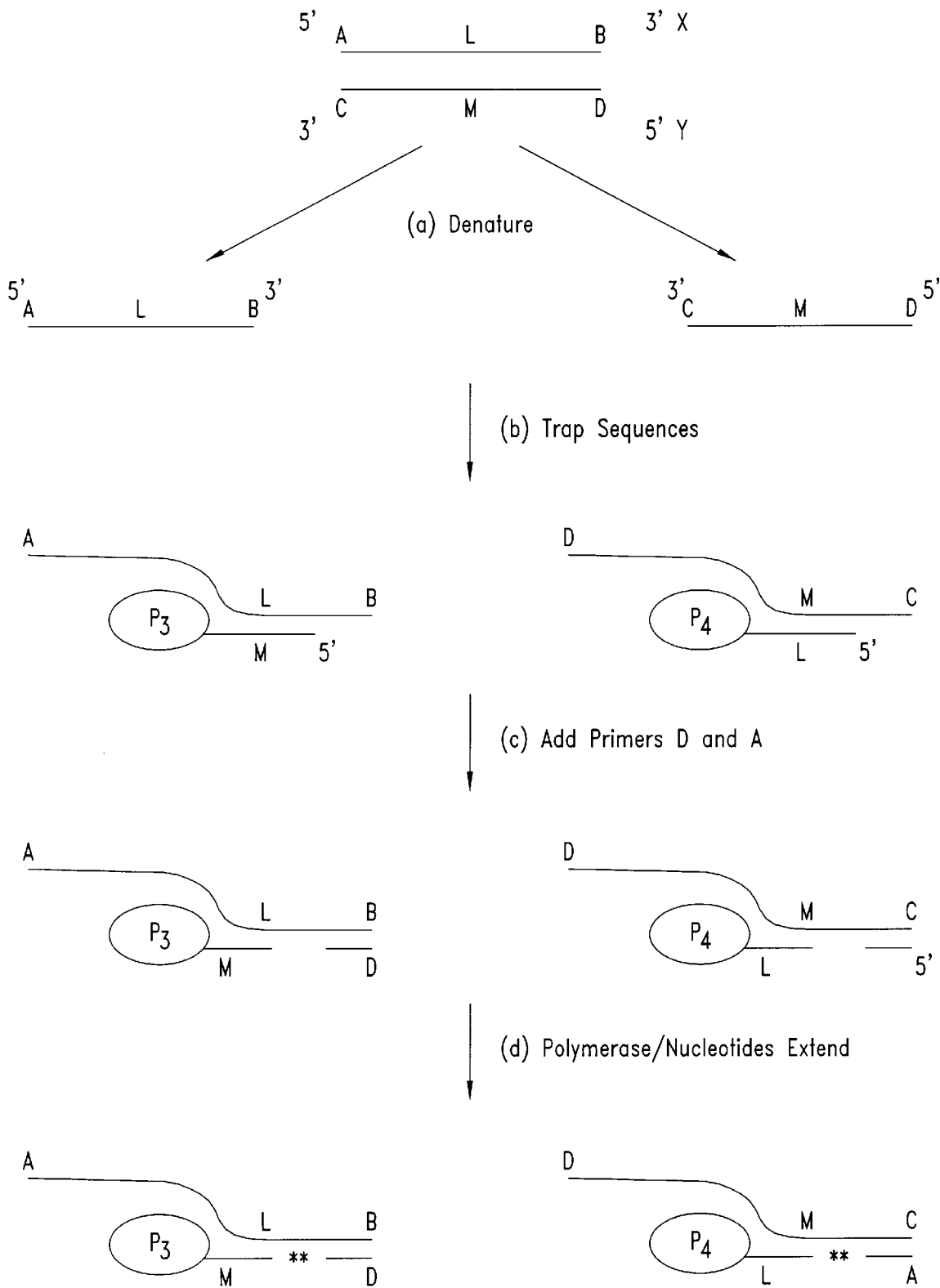
FIGS. 5A and 5B schematically illustrates a further procedure in accordance with the second embodiment of the invention.
Figure 5B:
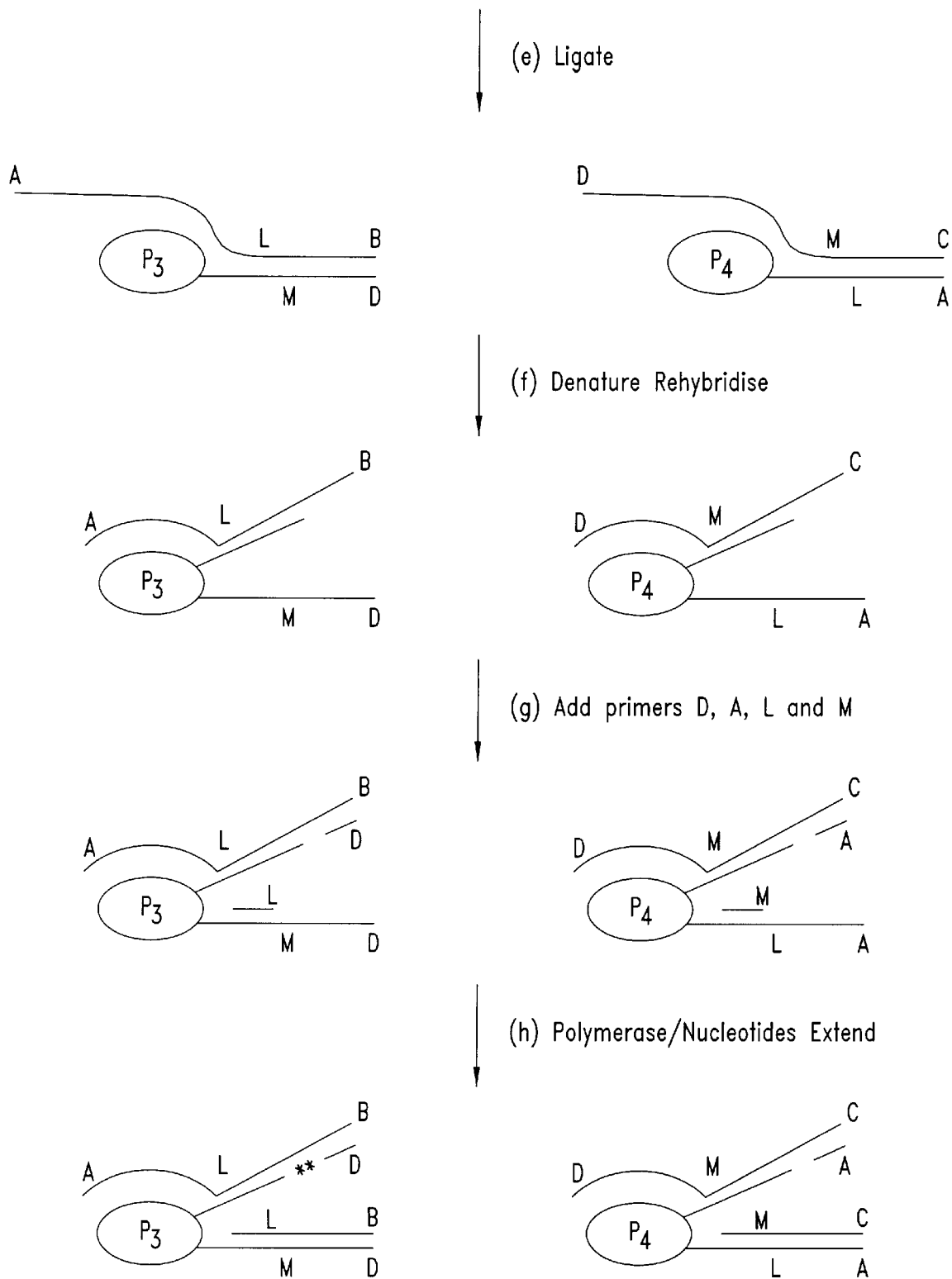
Figure 5C:
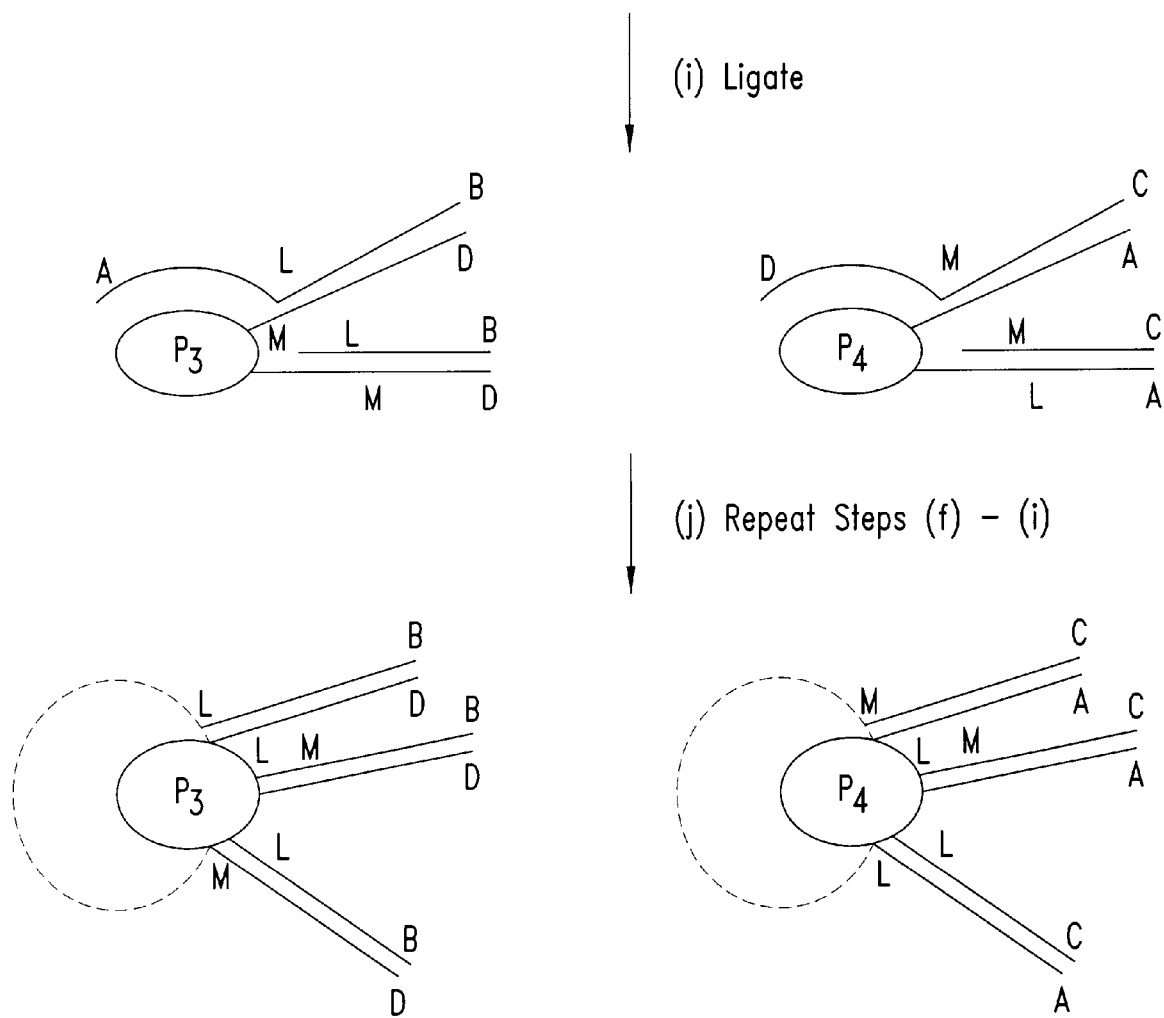

Reference is now made to FIG. 5 which illustrates a modification of the procedure of FIG. 4.

The method of FIG. 5 starts with the same double stranded nucleic acid as that of FIG. 3. Furthermore, the method of FIG. 5 uses two types of particle, namely particles P3 having oligonucleotides of sequence M immobilised thereon via their 3' ends, and particles P4 having oligonucleotides of sequence L immobilised thereon via their 3' ends.

The sequence of reactions for the method of FIG. 5 is the same as that for the method of FIG. 4. The product of the method of FIG. 5 comprises supports having immobilised copy target 1 strands of the sequences.

3' M-----------------D 5' and

3' L-----------------A 5'

These supports may be used for producing enhanced quantities of the sequences.

5' L------------------ B 3' and

5' M-------------------C 3' which are present in the original double stranded nucleic acid.

Figure 6A:
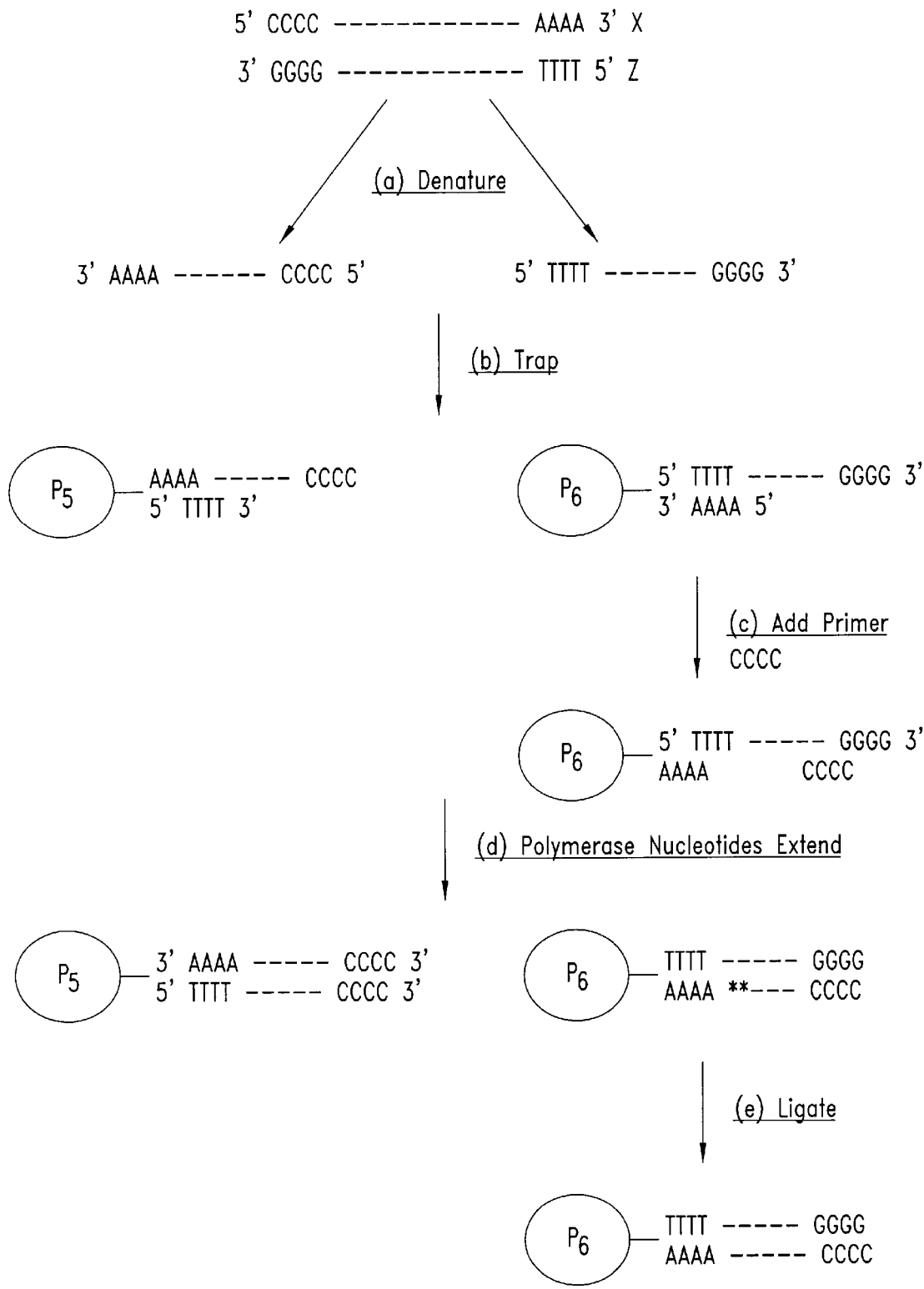
FIGS. 6A and 6B schematically illustrates a procedure in accordance with the third embodiment of the invention.
Figure 6B:
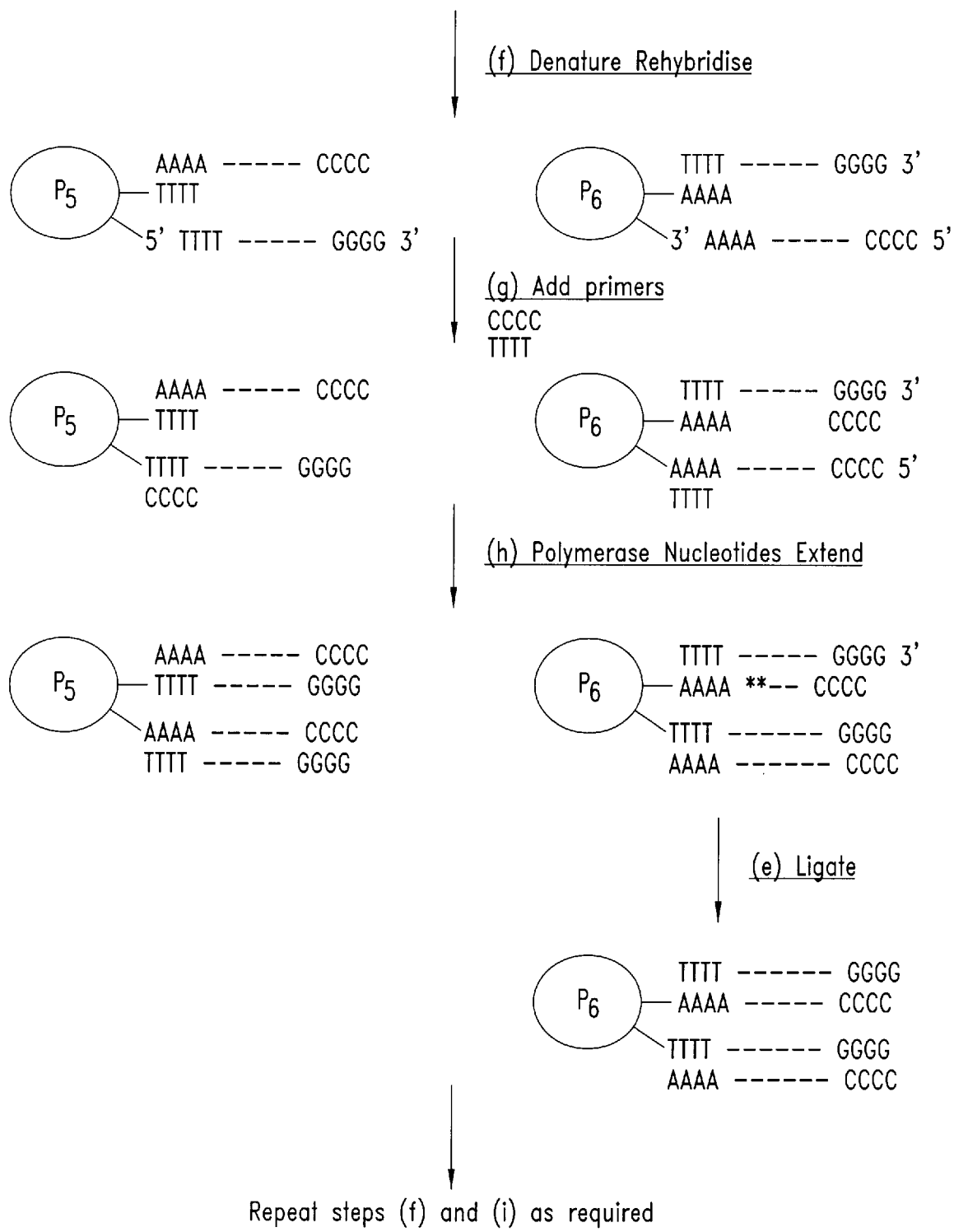

Reference is now made to FIG. 6 which depicts a method in accordance with the third embodiment of the invention which is, in effect, a combination of the methods illustrated in FIGS. 2 and 4. In the method of FIG. 6, a first type of particle P5 traps sequence X (of the original double stranded nucleic acid) by the 3' end thereof (cf particle P1 in FIG. 2). A second type of particle P6 traps sequence Y by the 5' end thereof (cf particle P4 in FIG. 4).

The overall reaction scheme is as depicted in FIG. 6. The sequence of reactions effected on particle P5 closely follows the sequence for particle P1. The sequence of reactions on P6 follows the sequence on particle P4. Although particles P5 and P6 are provided in the same column, the ligation reactions effected on P6 have no effect on P5.

The method of FIG. 6 produces a support which may be used for generating enhanced amounts of sequences X and Y as present in the original nucleic acid.

Figure 7A:
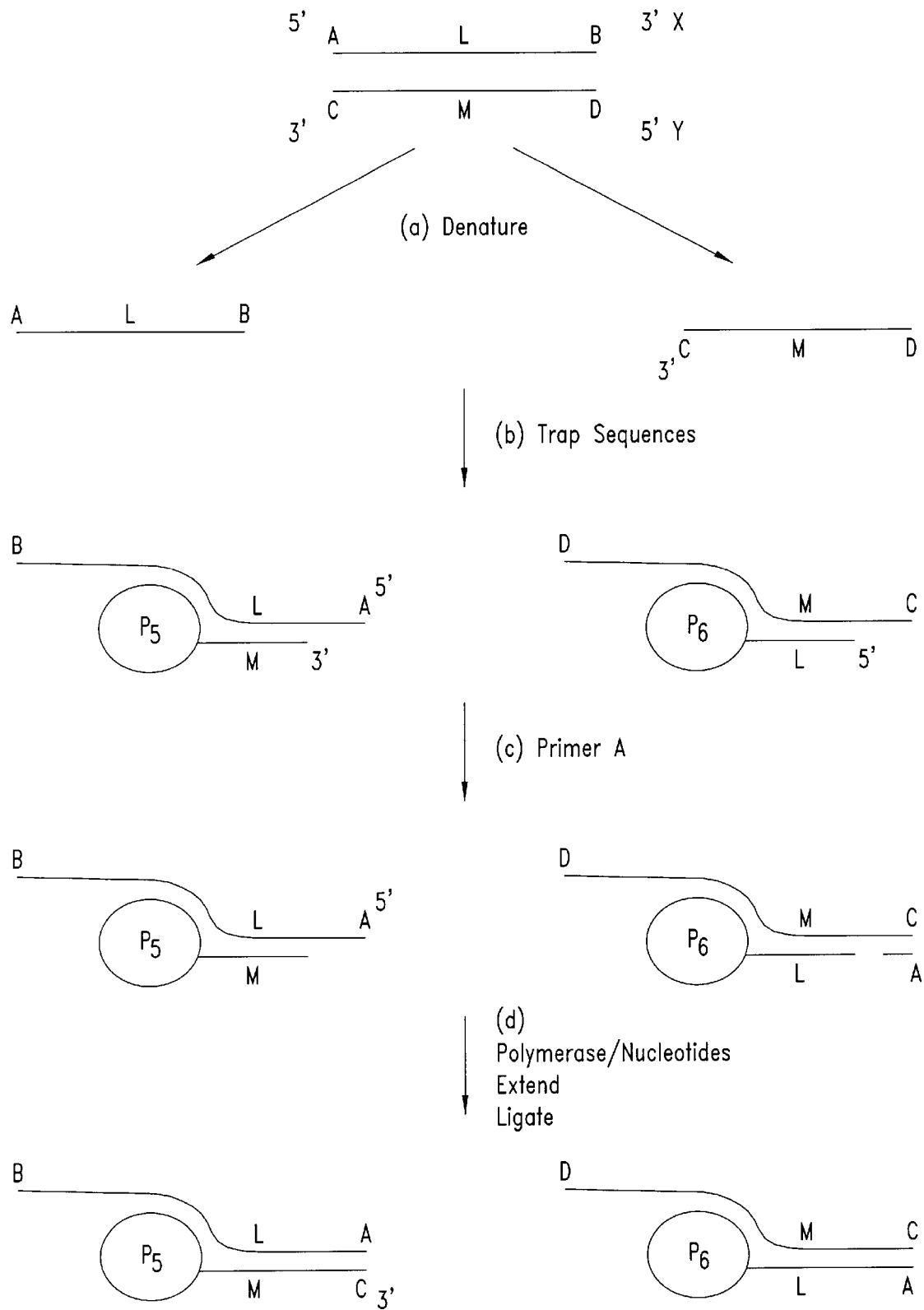
FIGS. 7A and 7B schematically illustrates a further procedure in accordance with the third embodiment of the invention.
Figure 7B:
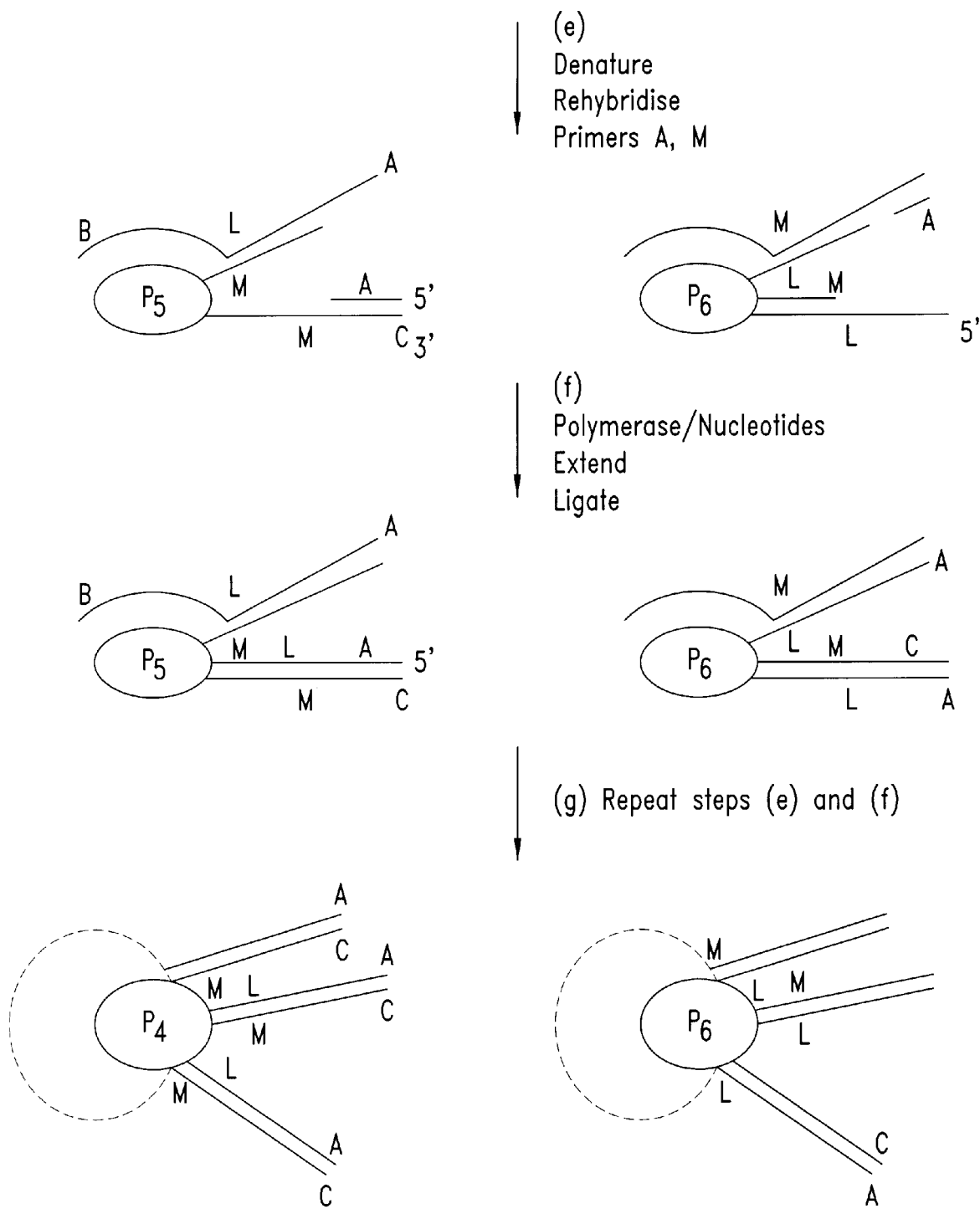

The method of FIG. 6 may be modified to operate as shown in FIG. 7 which starts with a nucleic acid of the type shown in FIG. 3. In FIG. 7, particles P5 have oligonucleotides of sequence M immobilised thereto via their 5' ends (cf particle P1 in FIG. 3) whereas particles P6 have oligonucleotides of sequence L immobilised thereto via their 3' ends (cf particle P4 in FIG. 5). The sequence of reactions in FIG. 7 is the same as that for FIG. 5 or FIG. 6. During this sequence, particles P5 function in the same way as particles P1 in FIG. 3 whereas particles P6 function in the same way as particles P4 in FIG. 5).

The method of FIG. 7 yields supports which may be used for producing enhanced quantities of sequences

3' M --------------------C 5' and

3' L--------------------A 5' as present in the original nucleic acid sample.

The invention is illustrated by way of example only with reference to the following non-limiting Examples.

EXAMPLE 1

In this Example, the term "buffer" refers to a composition comprising 10 mM Tris HCl pH 8.3, 50 mM KCl, and 1.5 mM MgCl$_2$.

A 24-mer oligonucleotide having the following sequence (I)

5' GGC GTA ATC ATG GTC ATA GCT GTT 3'            (I)

was immobilised via its 5' end on particulate supports (size 105 μm) available from 3M under the name M-phase via a siloxane matrix using the procedure described in WO-A-93/13220 (Tepnel). The particles comprised in excess of 50 μmoles (per gram of support) of sequence (I).

2 mg of the supports were placed in each of five flow through column arrangements having an internal diameter of 2 mm. The supports were retained in position by two frits located 10 mm apart.

25 fmol of a model 48-mer oligonucleotide having the sequence (II)

5' AGC GGA TAA CAA TTT CAC ACA GGA AAC            (II)
AGC TAT GAC CAT GAT TAC GCC 3' contained in the buffer was then introduced into each of the columns which were then initially maintained at 95° C. for 10 minutes. The temperature was then reduced to 72° C. This procedure resulted in hybridisation of sequence (II) at the immobilised sequence (I).

The column was then washed with buffer, the temperature reduced to 57° C. and further buffer added containing 0.2 mM of each of the tour dNTPs and 1.25 units polymerase enzyme (Thermas aquaticus) were added to the column.

The column was maintained at 57° C. for 2 minutes to extend the immobilised 24-mer oligonucleotide (sequence (I)) using the hybridised 48-mer oligonucleotide as a template.

The temperature of the column was then increased to 95° C. for 2 minutes to denature the 48-mer sequence (II) from the extended sequence (I).

The column was then cooled to 72° C. and buffer containing 0.2 mM of each of the four dNTPs, 1.25 units polymerase enzyme (Thermus aquaticus) and 25 pmol of a biotinylated 24-mer oligonucleotide having the sequence (III)

5' AGC GGA TAA CAA TTT CAC ACA GGA 3'            (III)

was then introduced on to the column which was maintained at 72° C. for two minutes so as to hybridise sequences II to non-extended sequences (I) and to hybridise sequences (III) to the extended sequences (I). The column was then cooled to a temperature of 57° C. which was maintained for two minutes so as to permit extension of sequences (I) and (III).

The supports in one of the columns were then collected for use in the detection procedure described below.

The remaining columns were then subjected to cycles of denaturation at 95° C. (for 2 minutes), addition of further sequences (II) and rehybridisation at 72° C. (for 2 minutes), and extension at 57° C. (for 2 minutes) (although shorter times could be used) using the procedures outlined in more detail above. Supports were collected after four, nine, nineteen and twenty nine such further cycles. (Such samples had therefore been subjected to a total of five, ten, twenty and thirty extension reactions respectively).

A blank experiment was also performed in the following way (a) One column contained supports with immobilised sequences (I) and buffer. The column was cycled through the above procedures without addition of further nucleic acid or reagents.

All collected samples were subjected to the following detection procedure.

Figure 8:
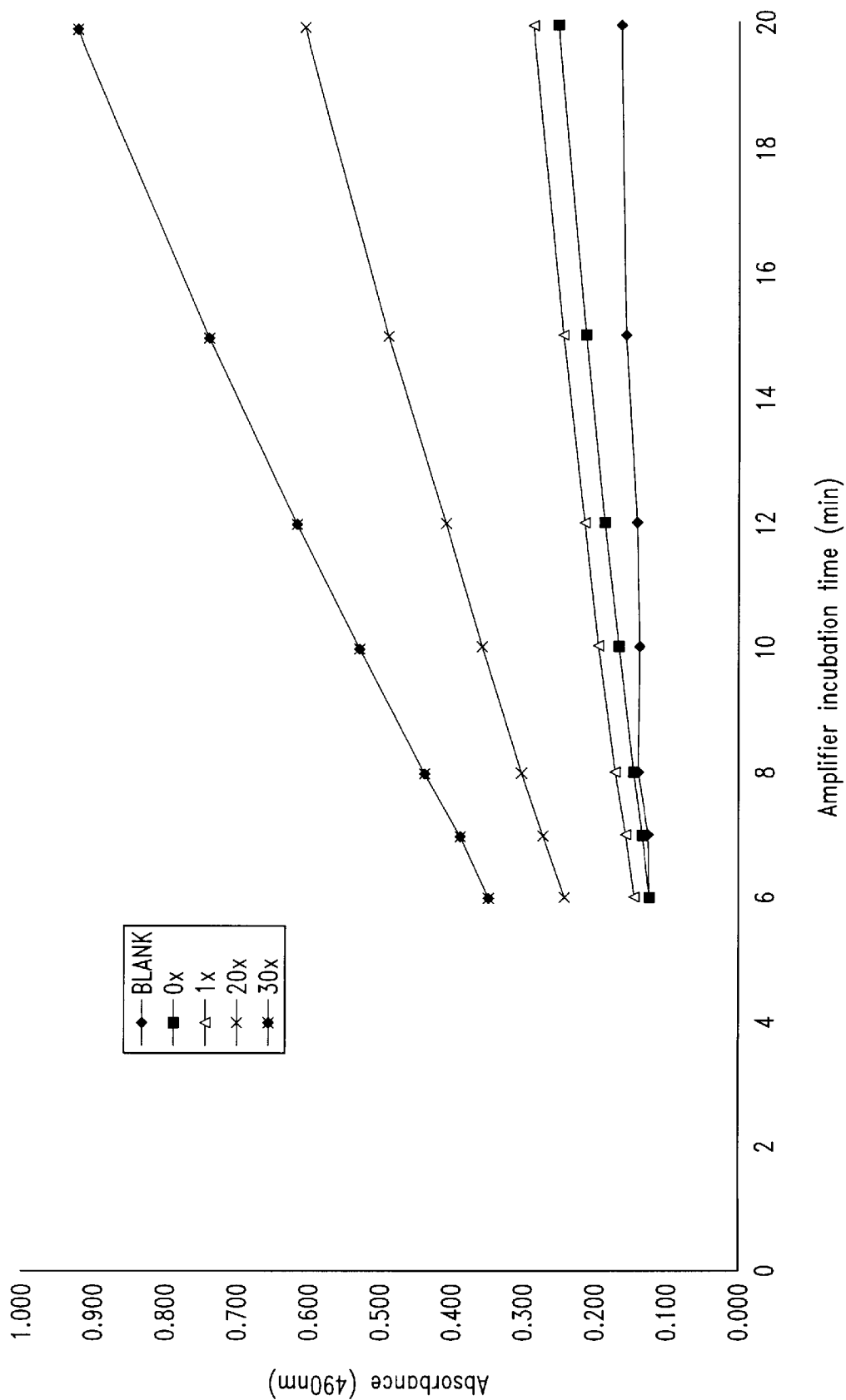
FIGS. 8 and 9 are graphs illustrating the results of Example 1.
Figure 9:
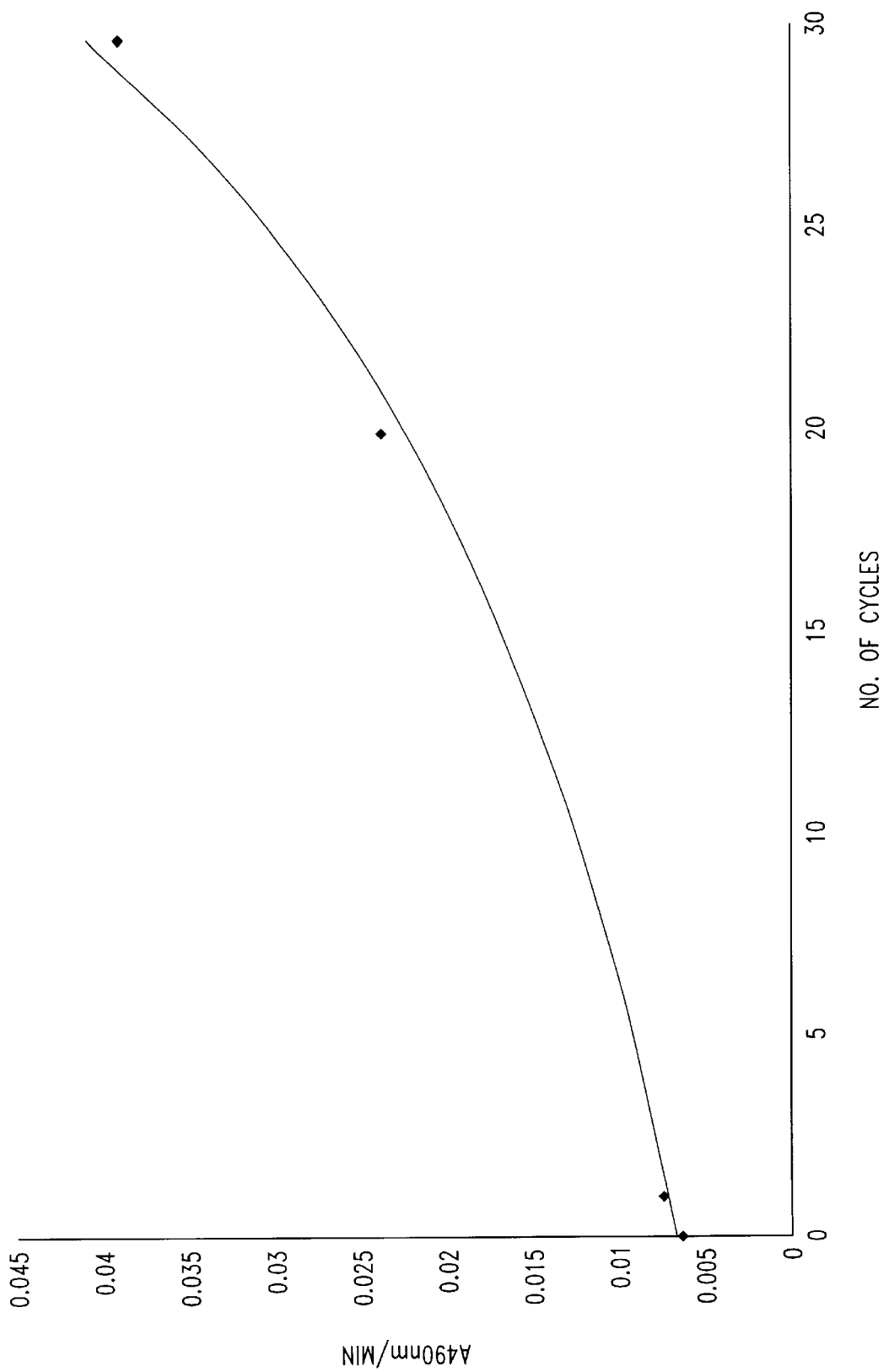

The collected particles were reacted with streptavidin Alkaline Phosphatase conjugate. Excess conjugate was removed by washing and the particles were then treated with a commercially available alkaline phosphatase detection system (Ampak, ex Dako). This developed a colour which was monitored at 490 nm with time. The result is shown in FIG. 8 which is a plot of absorbance vs amplifier incubation time. FIG. 9 is a plot of rate of change of the absorbance vs number of extension cycles to which the sample had been subject.

From this data, it can clearly be seen that the amplification is exponential.

EXAMPLE 2

The procedure of Example 1 was repeated save that sequences (I), (II), and (III) were replaced by the following sequences (Ia), (IIa), (IIIa), respectively

```
5' AGC GGA TAA CAA TTT CAC ACA GGA 3'            (Ia)

5' GGC GTA ATC ATG GTC ATA GCT GTT TCC           (IIa)
   TGT GTG AAA TTG TTA TCC GCT 3'

5' GGC GTA ATC ATG GTC ATA GCT GTT 3'            (IIIa)
```

Additionally control experiments were carried out as follows:

(b) One column containing extended sequence (I) was probed with a non-complementary (to sequence (I)) biotinylated 24 mer oligonucleotide having the sequence;

```
5' CGC CAT TCA GGC TGC GCA ACT GTT 3'
```

The column was cycled 30 times.

(c) One column containing supports with extended immobilised sequences (I) was maintained at 4° C. as a zero cycle control.

Figure 10:
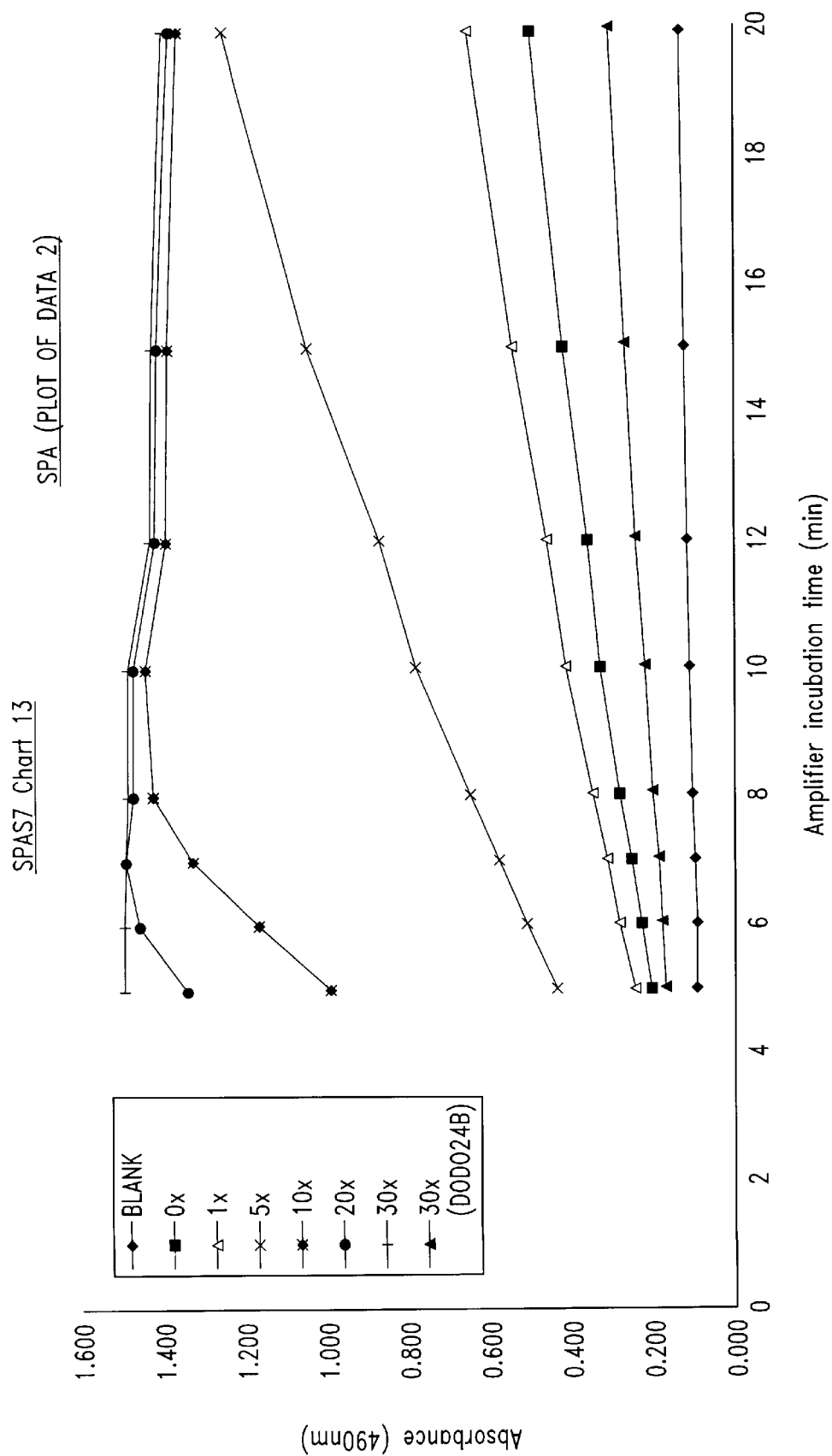
FIGS. 10 and 11 are graphs illustrating the results of Example 2.
Figure 11:
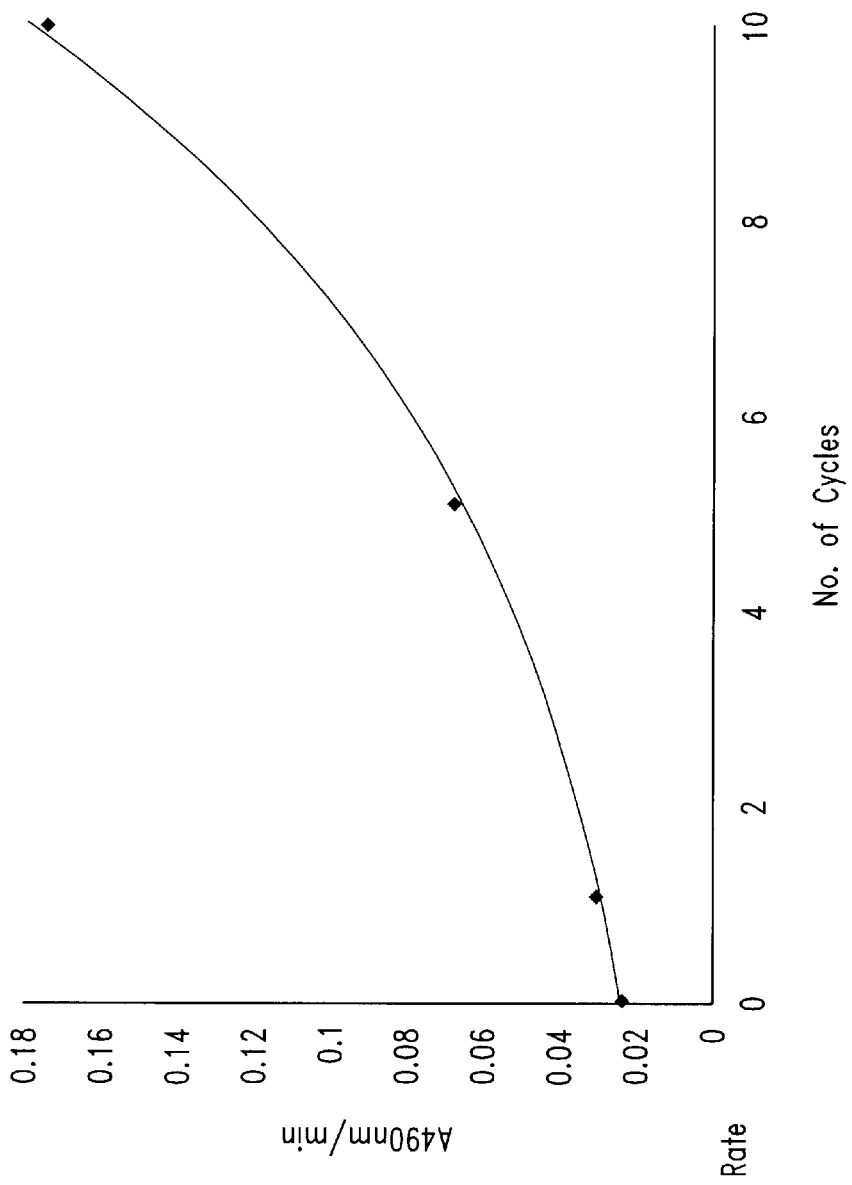

The results are plotted in FIGS. 10 and 11 respectively. Once again, it can be seen that the amplification is exponential.

It will be appreciated that sequences (II) and (IIa) are complementary. It is therefore possible to use a combination of particles provided with immobilised sequences (I) and particles provided with immobilised sequences (Ia) to effect amplification of the sequences (II) and (IIa).

I claim:

1. A method of producing copies of at least part of a target nucleic acid strand present or potentially present in a sample, the method comprising the steps of (i) providing a solid support system having covalently linked thereon a plurality of single stranded oligonucleotides which are capable of hybridizing to the target strands, (ii) providing the target strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 strands which incorporate the covalently linked oligonucleotides and include a nucleic acid sequence complementary to at least part of the target strand, wherein the production of said copy target 1 strands comprises a primer extension step in which the target strand is used as a template to generate at least part of the copy target 1 sequence, (iv) denaturing the target strands hybridized to the copy target 1 strands, (v) simultaneously or sequentially in either order,
(a) hybridizing primers to the copy target 1 strands immobilized on the solid support, and
(b) hybridizing the denatured target strands to oligonucleotides on the support which have not been converted to copy target 1 strands, (vi) simultaneously,
(a) producing copy target 2 strands which comprise a nucleic acid sequence of interest from the primers hybridized to the copy target 1 strands, wherein the production of copy target 2 strands comprises a primer extension step; and
(b) producing further copy target 1 strands from the target strands hybridized to oligonucleotides on the support, wherein the production of further copy target 1 strands comprises a primer extension step;

(vii) denaturing the copy target 2 strands hybridized to the copy target 1 strands and rehybridizing the copy target 2 strands to oligonucleotides on the support which have not been converted to copy target 1 strands, (viii) hybridizing primers to the copy target 1 strands immobilized on the solid support, (ix) simultaneously,
(a) producing copy target 2 strands which comprise the nucleic acid sequence of interest from the primers hybridised to the copy target 1 strands, wherein the production of copy target 2 strands comprises a primer extension step; and
(b) producing further copy target 1 strands from copy target 2 strands hybridized to the oligonucleotides on the support, wherein the production of further copy target 1 strands comprises a primer extension step; and (x) repeating steps (vii)–(ix) as many times as required in order to produce copies of at least part of the target nucleic acid strand.

2. A method of producing copies of at least part of a target nucleic acid strand present or potentially present in a sample, the method comprising the steps of (i) providing a solid support system having covalently linked thereon a plurality of single stranded oligonucleotides which are capable of hybridizing to the target strands, (ii) providing the target strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 strands which incorporate the covalently linked oligonucleotides and include a nucleic acid sequence complementary to at least part of the target strand, wherein the production of said copy target 1 strands comprises a primer extension step in which the target strand is used as a template to generate at least part of the copy target 1 sequence, (iv) denaturing the target strands hybridized to the copy target 1 strands, (v) rehybridizing the denatured target strands to oligonucleotides on the support which have not been converted to copy target 1 strands and producing therefrom further copy target 1 strands, (vi) hybridizing primers to the copy target 1 strands immobilized on the solid support and producing therefrom copy target 2 strands which comprise a nucleic acid sequence of interest, (vii) denaturing the copy target 2 strands hybridized to the copy target 1 strands and rehybridizing the copy target 2 strands to oligonucleotides on the support which have not been converted to copy target 1 strands, (viii) hybridizing primers to the copy target 1 strands immobilized on the solid support, (ix) simultaneously
  (a) producing copy target 2 strands which comprise the nucleic acid sequence of interest from the primers hybridized to the copy target 1 strands, wherein the production of copy target 2 strands comprises a primer extension step; and
  (b) producing further copy target 1 strands from copy target 2 strands hybridized to the oligonucleotides on the support, wherein the production of further copy target 1 strands comprises a primer extension step; and (x) repeating steps (vii)–(ix) as many times as required in order to produce copies of at least part of the target nucleic acid strand.

3. A method of producing copies of at least part of a target nucleic acid strand present or potentially present in a sample, the method comprising the steps of (i) providing a solid support system having covalently linked thereon a plurality of single stranded oligonucleotides which are capable of hybridizing to the target strands, (ii) providing the target strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 strands which incorporate the covalently linked oligonucleotides and include a nucleic acid sequence complementary to at least part of the target strand, wherein the production of said copy target 1 strands comprises a primer extension step in which the target strand is used as a template to generate at least part of the copy target 1 sequence, (iv) denaturing the target strands hybridized to the copy target 1 strands, (v) washing the support system to remove said target strands, (vi) hybridizing primers to the copy target 1 strands immobilized on the solid support and producing therefrom copy target 2 strands which comprise a nucleic acid sequence of interest, and (vii) denaturing the copy target 2 strands hybridized to the copy target 1 strands and rehybridizing the copy target 2 strands to oligonucleotides on the support which have not been converted to copy target 1 strands, (viii) hybridizing primers to the copy target 1 strands immobilized on the solid support, (ix) simultaneously
  (a) producing copy target 2 strands which comprise the nucleic acid sequence of interest from the primers hybridized to the copy target 1 strands, wherein the production of copy target 2 strands comprises a primer extension step; and
  (b) producing further copy target 1 strands from copy target 2 strands hybridized to the oligonucleotides on the support, wherein the production of further copy target 1 strands comprises a primer extension step; and (x) repeating steps (vii)–(ix) as many times as required in order to produce copies of at least part of the target nucleic acid strand.

4. A method of producing copies of at least part of a nucleic acid strand present or potentially present in a sample, the method comprising the steps of (i) providing a solid support system having covalently linked thereon a plurality of each of two different single stranded oligonucleotides 0 and 0' each of which is capable of hybridizing to a respective one of two complementary strands of a double stranded nucleic acid, said complementary stands providing target 1 and 1' strands, (ii) providing the target 1 and 1' strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 and 1' strands each of which incorporates an covalently linked oligonucleotide 0 or 0' respectively, and a nucleic acid sequence complementary to at least part of the target 1 or 1' strand respectively, wherein the production of said copy target 1 and 1' strands comprises a primer extension step in which the respective target strands are used as templates to generate at least part of the copy target 1 or 1' sequence, (iv) denaturing the target 1 and 1' strands hybridised to the copy target 1 and 1' strands and rehybridizing at least some of the target 1 and 1' strands to oligonucleotides on the support which have not been converted to copy target 1 or 1' strands, (v) hybridizing primers to the copy target 1 and 1' strands immobilized on the solid support, (vi) simultaneously,
  (a) producing copy target 2 and 2' strands respectively from the primers hybridized to the copy target 1 and 1' strands, wherein the production of copy target 2 and 2' strands comprises a primer extension step; and
  (b) producing further copy target 1 and 1' strands from target 1 and 1' strands hybridized to the immobilized oligonucleotides, wherein the production of copy target 1 and 1' strands comprises a primer extension step;

(vii) denaturing the copy target 2 and 2' strands hybridised to the copy target 1 and 1' strands and rehybridizing the copy target 2 and 2' strands to oligonucleotides on the support which have not been converted to copy target strands, (viii) hybridizing primers to the copy target 1 and 1' strands immobilized on the solid support, (ix) simultaneously
  (a) producing copy target 2 and 2' strands which comprise the nucleic acid sequence of interest from the primers hybridized to the copy target 1 and 1' strands, wherein the production of copy target 2 and 2' strands comprises a primer extension step; and
  (b) producing further copy target 1 and 1' strands from the copy target 2 and 2' strands hybridized to oligonucleotides on the support, wherein the production of copy target 1 and 1' strands comprises a primer extension step, and (x) repeating steps (vii)–(ix) as many times as required in order to produce copies of at least part of the target nucleic acid strand.

5. A method as claimed in any one of claims 1, 2 or 3 wherein the solid support system comprises particles, the oligonucleotides being covalently linked onto the particles.

6. A method as claimed in claim 5 wherein the particles are of non-porous silica.

7. A method as claimed in claim 5 wherein the particles have a size of 50 to 200 microns.

8. A method as claimed in any one of claims 1, 2 or 3 wherein the oligonucleotides are bonded to the support via a siloxane matrix.

9. A method as claimed in any one of claims 1, 2 or 3 wherein the solid support is provided in a column into and from which liquid may be readily introduced and removed.

10. A method as claimed in any one of claims 1, 2 or 3 wherein all or substantially all of the original oligonucleotides covalently linked onto the supports are converted to copy target 1 strands.

11. A method as claimed in any one of claims 1, 2 or 3 wherein the orientation of the oligonucleotides on the support is such that they may be extended using the target strand or copy target 2 strand hybridized thereto as a template so as to produce the copy target 1 strand.

12. A method as claimed in any one of claims 1, 2 or 3 wherein the solid support system incorporates two different covalently linked oligonucleotides each orientated as specified in claim 10, one oligonucleotide being such that it will hybridize to the target strand.

13. A method as claimed in claim 1 wherein copy target 1 strands are produced by hybridizing a primer to the target or copy target 2 strands hybridized to the covalently linked oligonucleotide, and then extending the primer, in steps (v)(b) and (vii)(b), towards the oligonucleotide to which it is then ligated to complete preparation of the copy target 1 strand.

14. A method as claimed in any one of claims 1, 2 or 3 wherein the plurality of single stranded oligonucleotides comprises (i) a first oligonucleotide that is bonded via its 5' end to the solid support system, and (ii) a second oligonucleotide that is bonded via its 3' end to the solid support system.

15. A method as claimed in any one of claims 1, 2, 3 or 4 further comprising the steps of (vii) hybridizing primers to the copy target 1 strands at locations such that extension products of the primers using the copy target 1 strands as templates incorporate a sequence of interest, (viii) producing extension product strands by extending the primers using the copy target 1 strands as templates, and (ix) denaturing the extension product strands from the copy target 1 strands and collecting the extension product strands.

16. A method of producing copies of at least part of a target nucleic acid strand present or potentially present in a sample, the method comprising the steps of (i) providing a solid support system having covalently linked thereon a plurality of single stranded oligonucleotides which are capable of hybridizing to the target strands, (ii) providing the target strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 strands which incorporate the covalently linked oligonucleotides and include a nucleic acid sequence complementary to at least part of the target strand, wherein the production of said copy target 1 strands comprises a primer extension step in which the target strand is used as a template to generate at least part of the copy target 1 sequence, (iv) denaturing the strands hybridized to the copy target 1 strands and rehybridising at least some of the target strands to oligonucleotides on the support which have not been converted to copy target 1 strands, (v) hybridizing primers to copy target 1 strands immobilized on the solid support, (vi) simultaneously
  (a) producing copy target 2 strands which comprise the nucleic acid sequence of interest from the primers hybridized to copy target 1 strands, wherein the production of copy target 2 strands comprises a primer extension step; and
  (b) producing further copy target 1 strands from target strands hybridized to the immobilized oligonucleotides, wherein the production of further copy target 1 strands comprises a primer extension step;

(vii) denaturing the copy target 2 strands hybridized to the copy target 1 strands and rehybridizing the copy target 2 strands to oligonucleotides on the support which have not been converted to copy target strands, (viii) hybridizing primers to the copy target 1 strands immobilized on the solid support, (ix) simultaneously,
  (a) producing copy target 2 strands which comprise the nucleic acid sequence of interest from the primers hybridized to the copy target 1 strands, wherein the production of copy target 2 strands comprises a primer extension step; and
  (b) producing further copy target 1 strands from the copy target 2 strands hybridized to oligonucleotides on the support, wherein the production of further copy target 1 strands comprises a primer extension step;

(x) repeating steps (vii)–(ix) as many times as required, (xi) hybridizing primers to the copy target 1 strands at locations such that extension products of the primers using the copy target 1 strands as templates incorporate the sequence of interest, (xii) extending the primers using the copy target 1 strands as templates, and (xiii) denaturing the product strands from the copy target 1 strands and collecting the product strands.

17. A method as claimed in claim 2 or claim 3 wherein copy target 1 strands are produced by hybridizing a primer to the target or copy target 2 strands hybridized to the covalently linked oligonucleotide, and then extending the primer towards the oligonucleotide to which it is then ligated to complete preparation of the copy target 1 strand.

18. A method of producing copies of at least part of a nucleic acid strand present or potentially present in a sample, the method comprising the steps of (i) providing a solid support system having covalently linked thereon a plurality of each of two different single stranded oligonucleotides 0 and 0' each of which is capable of hybridizing to a respective one of two complementary strands of a double stranded nucleic acid, said complementary strands providing target 1 and 1' strands, (ii) providing the target 1 and 1' strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 and 1' strands each of which incorporates covalently linked oligonucleotide 0 or 0' respectively, and a nucleic acid sequence complementary to at least part of the target 1 or 1' strand respectively, wherein the production of said copy target 1 and 1' strands comprises a primer extension step in which the respective target strands are used as templates to generate at least part of the copy target 1 or 1' sequence, (iv) denaturing the target 1 and 1' strands hybridized to the copy target 1 and 1' strands and washing the support system to remove the target 1 and 1' strands, (v) hybridizing primers to the copy target 1 and 1' strands immobilized on the solid support, (vi) producing copy target 2 and 2' strands, respectively, from the primers hybridized to the copy target 1 and 1' strands, wherein the production of copy target 2 and 2' strands comprises a primer extension step;

(vii) denaturing the copy target 2 and 2' strands hybridized to the copy target 1 and 1' strands and rehybridizing the copy target 2 and 2' strands to oligonucleotides on the support which have not been converted to copy target strands, (viii) hybridizing primers to the copy target 1 and 1' strands immobilized on the solid support, (ix) simultaneously,
 (a) producing copy target 2 and 2' strands which comprise the nucleic acid sequence of interest from the primers hybridized to the copy target 1 and 1' strands, wherein the production of copy target 2 and 2' strands comprises a primer extension step; and
 (b) producing further copy target 1 and 1' strands from the copy target 2 and 2' strands hybridized to oligonucleotides on the support, wherein the production of copy target 1 and 1' strands comprises a primer extension step; and (x) repeating steps (vii)–(ix) as many times as required in order to produce copies of at least part of the target nucleic acid strand.

19. A method of producing copies of at least part of a target nucleic acid strand present or potentially present in a sample, the method comprising the steps of (i) providing a solid support system having covalently linked thereon a plurality of single stranded oligonucleotides which are capable of hybridizing to the target strands, (ii) providing the target strands in single stranded form and hybridizing the target strands to oligonucleotides on the support, the number of oligonucleotides exceeding the number of target strands by at least a factor of 10, (ii)(a) washing the support system to remove non-hybridized material, (iii) producing copy target 1 strands which incorporate the covalently linked oligonucleotides and include a nucleic acid sequence complementary to at least part of the target strand, wherein the production of said copy target 1 strands comprises a primer extension step in which the target strand is used as a template to generate at least part of the copy target 1 sequence, (iv) denaturing the strands hybridized to the copy target 1 strands and washing the support system to remove said target strands, (v) hybridizing primers to copy target 1 strands immobilized on the solid support, (vi) producing copy target 2 strands which comprise the nucleic acid sequence of interest from the primers hybridized to copy target 1 strands, wherein the production of copy target 2 strands comprises a primer extension step, and (vii) denaturing the copy target 2 strands hybridized to the copy target 1 strands and rehybridizing the copy target 2 strands to oligonucleotides on the support which have not been converted to copy target strands, (viii) hybridizing primers to the copy target 1 strands immobilized on the solid support, (ix) simultaneously,
 (a) producing copy target 2 strands which comprise the nucleic acid sequence of interest from the primers hybridized to the copy target 1 strands, wherein the production of copy target 2 strands comprises a primer extension step, and
 (b) producing further copy target 1 strands from the copy target 2 strands hybridized to oligonucleotides on the support, wherein the production of further copy target 1 strands comprises a primer extension step;

(x) repeating steps (vii)–(ix) as many times as required, (xi) hybridizing primers to the copy target 1 strands at locations such that extension products of the primers using the copy target 1 strands as templates incorporate the sequence of interest, (xii) extending the primers using the copy target 1 strands as templates, and (xiii) denaturing the product strands from the copy target 1 strands and collecting the product strands.

* * * * *